(12) United States Patent
Martin et al.

(10) Patent No.: US 6,846,810 B2
(45) Date of Patent: Jan. 25, 2005

(54) ANTIVIRAL NUCLEOSIDE DERIVATIVES

(75) Inventors: Joseph Armstrong Martin, Menlo Park, CA (US); Keshab Sarma, Sunnyvale, CA (US); David Bernard Smith, San Mateo, CA (US); Mark Smith, San Francisco, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 10/717,260

(22) Filed: Nov. 19, 2003

(65) Prior Publication Data

US 2004/0121980 A1 Jun. 24, 2004

Related U.S. Application Data

(60) Provisional application No. 60/427,447, filed on Nov. 19, 2002, and provisional application No. 60/483,970, filed on Jul. 1, 2003.

(51) Int. Cl.$^7$ ............... A61K 31/7068; A61K 31/7052; A61K 31/70; C07H 19/067

(52) U.S. Cl. ............... 514/49; 514/934; 514/894; 536/28.51; 536/28.5; 536/55.3

(58) Field of Search ............... 514/49, 934, 894, 514/50; 536/28.51, 28.5

(56) References Cited

U.S. PATENT DOCUMENTS

| | | | |
|---|---|---|---|
| 3,998,807 A | | 12/1976 | Moffatt |
| 4,957,924 A | | 9/1990 | Beauchamp |
| 5,216,142 A | | 6/1993 | Horrobin et al. |
| 5,449,664 A | * | 9/1995 | Verheyden et al. ........... 514/45 |
| 6,184,376 B1 | | 2/2001 | Leanna et al. |

FOREIGN PATENT DOCUMENTS

| | | |
|---|---|---|
| EP | 0 343 133 B1 | 11/1989 |
| EP | 0 375 329 B1 | 6/1990 |
| WO | WO 93/07163 A1 | 4/1993 |
| WO | WO 94/22887 A1 | 10/1994 |
| WO | WO 94/24134 A1 | 10/1994 |
| WO | WO 00/23454 A1 | 4/2000 |
| WO | WO 01/45509 A1 | 6/2001 |
| WO | WO 01/68034 A2 | 9/2001 |
| WO | WO 01/90121 A2 | 11/2001 |
| WO | WO 02/100415 A2 * | 12/2002 |

OTHER PUBLICATIONS

Balimane, et al., "Direct Evidence for Peptide Transporter (PEPT1)–Mediated Uptake of a Nonpeptide Prodruc, Valacyclovir," Biochemical and Biophysical Research Communications, (1998) pp. 246–251, vol. 250, Article No. RC989298.

Beauchamp, et al., "Amino Acid Ester Prodrugs of Acyclovir," Antiviral Chemistry & Chemotherapy, (1992), pp. 157–164, 3(3).

Chamberlain, et al., "2'–Ester Prodrugs of the Varicella–Zoster Antiviral Agent, 6–Methoxypurine Arabinoside," Antiviral Chemistry & Chemotherapy, (1992), pp. 371–378, 3(6).

Harnden, et al., "Prodrugs of the Selective Antiherpesvirus Agent 9–[4–Hydroxy–3–(hydroxymethyl)but–1–yl]guanine (BRL 39123) with Improved Gastrointestinal Absorption Properties," J. Med. Chem., (1989), pp. 1738–1743, 32.

Hodge, et al., "Selection of an Oral Prodrug (BRL 42810; Famciclovir) for the Antiherpesvirus Agent BRL 39123 [9–4(–Hydroxy–3–Hydroxymethylbut–1–yl)Guanine; Penciclovir]," Antimicrobial Agents and Chemotherapy, (1989), pp. 1765–1773, 33(10).

Jones, et al. "Di– and Triester Prodrugs of the Varicella–Zoster Antiviral Agent 6–Methoxypurine Arabinoside," J. Med. Chem, (1992), pp. 56–63, 35.

Kim, et al., "Synthesis and Evaluation of 2–Amino–9–(1, 3–dihydroxy–2–propoxymethyl)–6–fluoropurine Mono– and Diesters as Potential Prodrugs of Ganciclovir," J. Med. Chem., (1999), pp. 324–328, 42.

Maag, Hans et al., "Synthesis and Anti–HIV Activity of 4'–Azido– and 4'–Methoxynucleosides," J. Med. Chem., (1992), pp. 1440–1451, 35.

Moffatt, J.G., "Chemical Transformations of the Sugar Moiety of Nucleosides", Nucleoside Analogues, (R. T. Walker, E. De Clercq, & F. Eckstein, eds.), (1979), pp. 71–164, Plenum Press, New York. (see p. 144).

(List continued on next page.)

Primary Examiner—James O. Wilson
Assistant Examiner—Michael C. Henry
(74) Attorney, Agent, or Firm—Brian L. Buckwalter

(57) ABSTRACT

The present invention relates to nucleoside derivatives for the treatment of Hepatitis C viral infections including compounds of formula I, pharmaceutical compositions comprising these compounds and methods for treatment or prophylaxis of Hepatitis C Virus mediated diseases employing said compounds in monotherapy or in combination therapy. The present invention further provides a process for preparing 1',3',4'-triacyl pyrimidine nucleoside from a N, 1',3',4'-tetraacylpyrimidine nucleoside

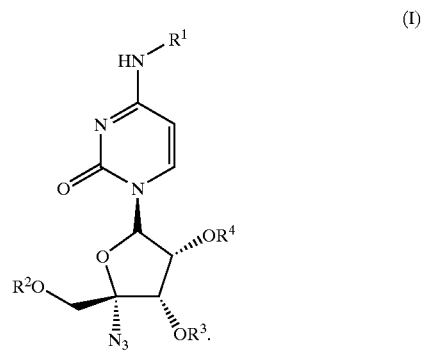

(I)

39 Claims, No Drawings

OTHER PUBLICATIONS

Nielsen, et al., "Human Peptide Transporters: Therapeutic Applications," Expert Opinion, Ther. Patents (2002), pp. 1329–1350, 12(9), Ashley Publications.

Pue, et al., "Pharmacokinetics of Famciclovir in Man," Antiviral Chemistry & Chemotherapy, (1993), pp. 47–55, 4, Suppl. 1.

Rubio–Aliaga, et al., "Mammalian Peptide Transporters as Targets for Drug Delivery," Trends in Pharmacological Sciences, (2002), pp. 434–440, 23(9).

* cited by examiner

ANTIVIRAL NUCLEOSIDE DERIVATIVES

CROSS REFERENCE TO PRIOR APPLICATIONS

This application claims benefit under Title 35 U.S.C. 119(e) of U.S. Provisional Application Nos. 60/427,447, filed Nov. 19, 2002 and 60/483,970, filed Jul. 1, 2003, which are hereby incorporated by reference in their entirety.

FIELD OF THE INVENTION

The invention relates to the field of antiviral therapy and in particular to nucleoside derivatives for treating Hepatitis C Virus (HCV) mediated diseases. The invention provides novel chemical compounds, pharmaceutical compositions comprising these compounds, methods for treatment or prophylaxis of HCV mediated diseases employing said compounds in monotherapy or in combination therapy.

BACKGROUND OF THE INVENTION

The invention relates to nucleoside derivatives as inhibitors of HCV replicon RNA replication. In particular, the invention is concerned with the use of pyrimidine nucleoside compounds as inhibitors of subgenomic HCV RNA replication and pharmaceutical compositions containing such compounds.

Hepatitis C virus is the leading cause of chronic liver disease throughout the world. Patients infected with HCV are at risk of developing cirrhosis of the liver and subsequent hepatocellular carcinoma and hence HCV is the major indication for liver transplantation. Only two approved therapies are currently available for the treatment of HCV infection (R. G. Gish, *Sem. Liver. Dis.*, 1999 19:5). These are interferon-α monotherapy and, more recently, combination therapy of the nucleoside analogue, ribavirin (Virazole), with interferon-α.

Many of the drugs approved for the treatment of viral infections are nucleosides or nucleoside analogues and most of these nucleoside analogue drugs are converted into the corresponding triphosphate in vivo. The triphosphates inhibit viral polymerase enzymes which halts viral replication. This conversion to the triphosphate is commonly mediated by cellular kinases and therefore the direct evaluation of nucleosides as inhibitors of HCV replication is only conveniently carried out using a cell-based assay. For HCV the availability of a true cell-based viral replication assay or animal model of infection is lacking.

Hepatitis C virus belongs to the family of Flaviridae. It is an RNA virus, the RNA genome encoding a large polyprotein that after processing produces the necessary replication machinery to ensure synthesis of progeny RNA. It is believed that most of the non-structural proteins encoded by the HCV RNA genome are involved in RNA replication. Lohmann et al. [V. Lohmann et al., *Science*, 1999, 285:110–113] have described the construction of a Human Hepatoma (Huh7) cell line in which subgenomic HCV RNA molecules have been introduced and shown to replicate with high efficiency. It is believed that the mechanism of RNA replication in these cell lines is identical to the replication of the full length HCV RNA genome in infected hepatocytes. The subgenomic HCV cDNA clones used for the isolation of these cell lines have formed the basis for the development of a cell-based assay for identifying nucleoside analogue inhibitors of HCV replication.

U.S. application Ser. No. 10/167,106 filed Jun. 11, 2002 entitled "4'-Substituted Nucleoside Derivatives as Inhibitors of HCV RNA Replication", discloses compounds related to the present invention.

SUMMARY OF THE INVENTION

Nucleoside derivatives frequently exhibit high levels of biological activity; however, their practical utility is often limited by suboptimal physical properties and poor pharmacokinetics. The present invention relates to chemical derivatives of 4'-substituted nucleosides with improved physiochemical and pharmacokinetic properties. These derivatives more efficiently permeate the intestinal mucosa whereupon a variety of enzymes present in the cytoplasm, blood, or serum convert the derivative to the non-derivatized nucleoside. These "pronucleotides" can improve the properties such as activity, bioavailability or stability of the parent nucleotide. Administration of compounds of formula I to mammals infected by HCV inhibits subgenomic HCV replication in a hepatoma cell line.

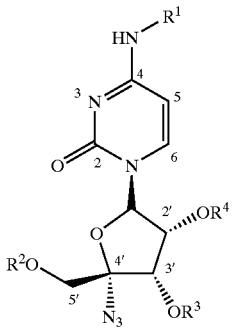

(I)

wherein:

$R^1$ and $R^2$ are independently selected from the group consisting of hydrogen, $COR^5$, $C(=O)OR^5$, $C(=O)SR^5$, $C(=O)NHR^5$ and $COCH(R^6)NHR^7$;

$R^3$ and $R^4$ independently of the other are selected from the group consisting of hydrogen, $COR^5$, $CO_2R^5$ and $COCH(R^6)NHR^7$, or $R^3$ and $R^4$ taken together are selected from the group consisting of $CH_2$, $C(CH_3)_2$ and CHPh;

$R^5$ is independently selected from the group consisting of $C_{1-18}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, alkyl substituted $C_{3-8}$ cycloalkyl, phenyl optionally independently substituted with one to three substituents selected from the group consisting of halo, lower alkyl, lower alkoxy, lower thioalkyl, lower alkyl sulfinyl, lower alkyl sulfonyl, nitro, and cyano, $CH_2Ph$ wherein in phenyl ring is optionally substituted as described above and $CH_2OPh$ wherein in phenyl ring is optionally substituted as described above;

$R^6$ is selected from the group consisting of the side chains of naturally occurring amino acids and $C_{1-5}$ unbranched or branched alkyl;

$R^7$ is selected from the group consisting of hydrogen, $R^5OCO$, and;

hydrates, solvates, clathrates and acid addition salts thereof; with the proviso that at least one of $R^1$, $R^2$, $R^3$, or $R^4$ is other than hydrogen.

The invention also provides methods of treating diseases mediated by Hepatitis C virus by administering a compound of formula I. The compound can be administered alone or in combination with an immune system modulator, an antiviral agent, or an anti-inflammatory agent. The invention further includes compositions for the treatment of treating diseases mediated by Hepatitis C virus by administering a therapeutically effective amount of a compound of formula I.

DETAILED DESCRIPTION OF THE INVENTION

Compounds of the present invention are pro-drugs or bioprecursors of the parent nucleoside and are converted in vivo to the compound of formula I wherein $R^1$, $R^2$, $R^3$, and $R^4$ are hydrogen. Pro-drugs include acyl derivatives, amino acid esters, alkoxycarbonyl, aryloxycarbonyl, thioalkylcarbonyl and arylthiocarbonyl nucleoside or pharmaceutically acceptable salts thereof.

One embodiment of the present invention is a nucleoside derivative according to formula I wherein $R^1$, $R^2$, $R^3$, $R^4$, $R^5$, $R^6$ and $R^7$ are independently selected from the groups defined hereinabove with the proviso that at least one of $R^1$, $R^2$, $R^3$, or $R^4$ is other than hydrogen.

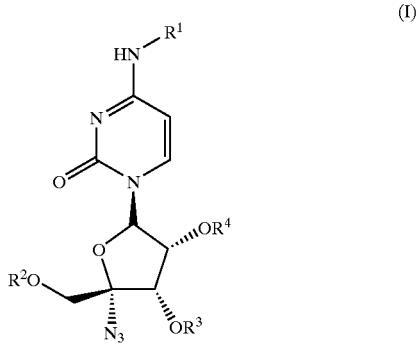

(I)

In another embodiment of the present invention there is provided a compound according to formula I wherein $R^1$, $R^2$, $R^3$, and $R^4$ each are independently $COR^5$, $C(=O)OR^5$ or $C(=O)SR^5$ and each $R^5$ is independently selected from the group consisting of $C_{1-18}$ unbranched or branched lower alkyl, phenyl and $CH_2OPh$.

In another embodiment of the present invention there is provided a compound according to formula I wherein $R^1$, $R^2$, $R^3$, and $R^4$ are $COR^5$ and each $R^5$ is independently selected from the group consisting of $C_{1-18}$ unbranched or branched lower alkyl, phenyl and $CH_2OPh$.

In another embodiment of the present invention there is provided a compound according to formula I wherein $R^1$ is $COR^5$, $C(=O)OR^5$, $C(=O)SR^5$ or $COCH(R^6)NHR^7$; $R^2$, $R^3$ and $R^4$ are hydrogen; and, $R^5$ or $R^6$ and $R^7$ are as defined hereinabove.

In another embodiment of the present invention there is provided a compound according to formula I wherein $R^1$ is $COR^5$, $C(=O)OR^5$, $C(=O)SR^5$ or $COCH(R^6)NHR^7$; $R^2$, $R^3$ and $R^4$ are hydrogen; $R^5$ is selected from a group consisting of $C_{1-18}$ unbranched or branched lower alkyl, $C_{3-8}$ cycloalkyl, phenyl and $CH_2OPh$ or $R^6$ is selected from the group consisting of $C_{1-5}$ unbranched or branched alkyl and the side chain of a naturally occurring amino acid and $R^7$ is as defined hereinabove.

In another embodiment of the present invention there is provided a compound according to formula I wherein $R^2$ is selected from the group consisting of $COR^5$, $C(=O)OR^5$, $C(=O)SR^5$ and $COCH(R^6)NHR^7$; $R^1$, $R^3$ and $R^4$ are hydrogen; and $R^5$ or $R^6$ and $R^7$ are as defined hereinabove.

In another embodiment of the present invention there is provided a compound according to formula I wherein $R^2$ is selected from the group consisting of $COR^5$, $C(=O)OR^5$, $C(=O)SR^5$ and $COCH(R^6)NHR^7$; $R^1$, $R^3$ and $R^4$ are hydrogen; $R^5$ is selected from the group consisting of is $C_{1-18}$ unbranched or branched alkyl, $C_{3-8}$ cycloalkyl and phenyl or $R^6$ is $C_{1-5}$ unbranched or branched alkyl or the side chain of a naturally occurring amino acid and $R^7$ are as defined hereinabove.

In another embodiment of the present invention there is provided a compound according to formula I wherein $R^2$ is $COCH(R^6)NH_2$; $R^1$, $R^3$, $R^4$ and $R^7$ are hydrogen; and, $R^6$ is selected from the group consisting of $C_{1-5}$ unbranched or branched alkyl or $CH_2Ph$.

In another embodiment of the present invention there is provided a compound according to formula I wherein $R^1$ and $R^2$ are independently selected from the group consisting of $COR^5$, $C(=O)OR^5$, $C(=O)SR^5$ and $COCH(R^6)NHR^7$; $R^3$ and $R^4$ are hydrogen; and, $R^5$ and/or $R^6$ and $R^7$ are independently selected from the group defined hereinabove.

In another embodiment of the present invention there is provided a compound according to formula I wherein $R^1$ is hydrogen; $R^2$, $R^3$ and $R^4$ are selected from the group consisting of $COR^5$, $C(=O)OR^5$ or $C(=O)SR^5$; and $R^5$ is independently selected from the group defined hereinabove.

In another embodiment of the present invention there is provided a compound wherein $R^1$ is hydrogen; $R^2$ is $COR^5$, $C(=O)OR^5$, $C(=O)SR^5$ or $COCH(R^6)NHR^7$; $R^3$ and $R^4$ taken together are selected from the group consisting of $CH_2$, $C(CH_3)_2$ and CHPh; and, $R^5$ or $R^6$ and $R^7$ are independently selected from the group hereinabove.

In another embodiment of the present invention there is provided a compound according to formula I wherein $R^1$ and $R^2$ are hydrogen; $R^3$ and $R^4$ taken independently are selected from the group consisting of $COR^5$, $C(=O)OR^5$, $C(=O)SR^5$ and $COCH(R^6)NHR^7$; and, $R^5$ or $R^6$ and $R^7$ are independently selected from the group hereinabove.

In another embodiment of the present invention there is provided a compound according to formula 1 wherein $R^1$ and $R^2$ are selected from the group consisting of $COR^5$, $C(=O)OR^5$, $C(=O)SR^5$ and $COCH(R^6)NHR^7$; $R^3$ and $R^4$ taken together are selected from the group consisting of $CH_2$, $C(CH_3)_2$ and CHPh; $R^7$ is hydrogen or $C(=O)OR^5$; and $R^5$ and/or $R^6$ are independently selected from the group defined hereinabove.

In another embodiment of the present invention there is provided a compound selected from the group consisting of isobutyric acid (2R,3S,4R,5R)-5-(4-amino-2-oxo-2H-pyrimidin-1-yl)-2-azido-4-isobutyryloxy-2-isobutyryloxymethyl-tetrahydro-furan-3-yl ester; (S)-1-((3R,4S,5R)-5-Azido-3,4-bis-propionyloxy-5-propionyloxymethyl-tetrahydro-furan-2-yl)-2-oxo-1,2-dihydro-pyrimidin-4-yl-ammonium; chloride; (S)-1-((3R,4S,5R)-5-Azido-3,4-bis-pentanoyloxy-5-pentanoyloxymethyl-tetrahydro-furan-2-yl)-2-oxo-1,2-dihydro-pyrimidin-4-yl-ammonium; chloride; (S)-1-[(3R,4S,5R)-5-Azido-3,4-dihydroxy-5-(4-methyl-benzoyloxymethyl)-tetrahydro-furan-2-yl]-2-oxo-1,2-dihydro-pyrimidin-4-yl-ammonium; chloride; (S)-1-((3R,4S,5R)-5-azido-3,4-bis-hexanoyloxy-5-hydroxymethyl-tetrahydro-furan-2-yl)-2-oxo-1,2-dihydro-pyrimidin-4-yl-ammonium; methanesulfonate; (S)-1-((3R,4S,5R)-5-azido-5-hydroxymethyl-3,4-bis-pentanoyloxy-tetrahydro-furan-2-yl)-2-oxo-1,2-dihydro-pyrimidin-4-yl-ammonium; trifluoro-acetate; Tetradecanoic acid (2R,3S,4R)-5-((S)-4-amino-2-oxo-2H-pyrimidin-1-yl)-2-azido-3,4-dihydroxytetrahydro-furan-2-ylmethyl ester; (S)-1-((3R,4S,5R)-5-azido-3,4-bis-butyryloxy-5-hydroxymethyl-tetrahydro-furan-2yl)-2-oxo-1,2-dihydro-pyrimidin-4-yl-ammonium; trifluoro-acetate; and, (S)-1-((3R,4S,5R)-5-Azido-5-decyloxycarbonyloxymethyl-3,4-dihydroxy-tetrahydro-furan-2-yl)-2-oxo-1,2-dihydro-pyrimidin-4-yl-ammonium; trifluoro-acetate.

In another embodiment of the present invention there is provided a method for treating diseases mediated by HCV comprising administering to a mammal in need thereof a therapeutically effective quantity of a nucleoside derivatives according to formula I wherein $R^1$, $R^2$, $R^3$, $R^4$, $R^5$, $R^6$ and $R^7$ are as defined hereinabove.

In another embodiment of the present invention there is provided a method for treating diseases mediated by HCV comprising administering to a mammal in need thereof a therapeutically effective quantity of a compound according to formula I wherein $R^1$, $R^2$, $R^3$, or $R^4$ are each independently selected from the group consisting of $COR^5$, $C(=O)OR^5$ and $C(=O)SR^5$ and $R^5$ are independently selected from the group defined hereinabove.

In another embodiment of the present invention there is provided a method for treating diseases mediated by HCV comprising administering to a mammal in need thereof a therapeutically effective quantity of a compound according to formula I wherein $R^1$, $R^2$, $R^3$, or $R^4$ are each $COR^5$ and each $R^5$ is independently selected from the group consisting of $C_{1-18}$ unbranched or branched alkyl, phenyl and $CH_2OPh$.

In another embodiment of the present invention there is provided a method for treating diseases mediated by HCV comprising administering to a mammal in need thereof a therapeutically effective quantity of a compound according to formula I wherein $R^1$ is selected from the group consisting of $COR^5$, $CO_2R^5$, $C(=O)SR^5$ and $COCH(R^6)NHR^7$; $R^2$, $R^3$, and $R^4$ are each hydrogen; and $R^5$ or $R^6$ and $R^7$ are as defined hereinabove.

In another embodiment of the present invention there is provided a method for treating diseases mediated by HCV comprising administering to a mammal in need thereof a therapeutically effective quantity of a compound according to formula I wherein $R^1$ is selected from the group consisting of $COR^5$, $C(=O)OR^5$, $C(=O)SR^5$ and $COCH(R^6)NHR^7$; $R^2$, $R^3$, and $R^4$ are each hydrogen; $R^5$ is selected from a group consisting of $C_{1-18}$ unbranched or branched lower alkyl, $C_{3-8}$ cycloalkyl, phenyl and $CH_2OPh$, or $R^6$ is selected from the group consisting of $C_{1-5}$ unbranched or branched alkyl and the side chain of a naturally occurring amino acid and $R^7$ is hydrogen.

In another embodiment of the present invention there is provided a method for treating diseases mediated by HCV comprising administering to a mammal in need thereof a therapeutically effective quantity of a compound according to formula I wherein $R^2$ is selected from the group consisting of $COR^5$, $C(=O)OR^5$, $C(=O)SR^5$ and $COCH(R^6)NHR^7$; $R^1$, $R^3$ and $R^4$ are hydrogen; and, $R^5$ or $R^6$ and $R^7$ are as defined hereinabove.

In another embodiment of the present invention there is provided a method for treating diseases mediated by HCV comprising administering to a mammal in need thereof a therapeutically effective quantity of a according to formula I wherein $R^2$ is selected from the group consisting of $COR^5$, $CO_2R^5$, and $COCH(R^6)NHR^7$; $R^1$, $R^3$ and $R^4$ are hydrogen; $R^5$ is selected from a group consisting of $C_{1-18}$ unbranched or branched alkyl, $C_{3-8}$ cycloalkyl, phenyl and $CH_2OPh$ or $R^6$ is $C_{1-5}$ unbranched or branched alkyl or the side chain of a naturally occurring amino acid and $R^7$ is hydrogen.

In another embodiment of the present invention there is provided a method for treating diseases mediated by HCV comprising administering to a mammal in need thereof a therapeutically effective quantity of a compound according to formula I wherein $R^2$ is $COCH(R^6)NHR^7$; $R^1$, $R^3$ and $R^4$ are hydrogen; $R^6$ is selected form the group consisting of $C_{1-5}$ unbranched or branched alkyl and $CH_2Ph$; and, $R^7$ is hydrogen.

In another embodiment of the present invention there is provided a method for treating diseases mediated by HCV comprising administering to a mammal in need thereof a therapeutically effective quantity of a compound according to formula I wherein $R^3$ and $R^4$ are hydrogen; and, $R^1$, $R^2$, $R^5$, $R^6$ and $R^7$ are independently selected from the groups defined hereinabove.

In another embodiment of the present invention there is provided a method for treating diseases mediated by HCV comprising administering to a mammal in need thereof a therapeutically effective quantity of a compound according to formula I wherein $R^1$ is hydrogen; $R^2$, $R^3$ and $R^4$ are independently selected from the group consisting of $COR^5$, $C(=O)OR^5$ and $C(=O)SR^5$ and, each $R^5$ is independently selected from the group defined hereinabove.

In another embodiment of the present invention there is provided a method for treating diseases mediated by HCV comprising administering to a mammal in need thereof a therapeutically effective quantity of a compound according to formula I wherein $R^1$ is hydrogen; $R^3$ and $R^4$, taken together, are selected from the group consisting of $CH_2$, $C(CH_3)_2$ and $CHPh$; $R^2$, $R^5$ or $R^6$ and $R^7$ are as defined hereinabove.

In another embodiment of the present invention there is provided a method for treating diseases mediated by HCV comprising administering to a mammal in need thereof a therapeutically effective quantity of a compound according to formula I wherein $R^1$ and $R^2$ are hydrogen; $R^3$, $R^4$, $R^5$ and/or $R^6$ and $R^7$ are independently selected from the group defined hereinabove.

In another embodiment of the present invention there is provided a method for treating diseases mediated by HCV comprising administering to a mammal in need thereof a therapeutically effective quantity of a compound according to formula I wherein $R^3$ and $R^4$ taken together are selected from the group consisting of $CH_2$, $C(CH_3)_2$ and $CHPh$; $R^1$, $R^2$, $R^5$ and/or $R^6$ and $R^7$ are independently selected from the group defined hereinabove.

In another embodiment of the present invention there is provided a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in a dose between 1 and 100 mg/kg of body weight per day.

In another embodiment of the present invention there is provided a method for treating diseases mediated by HCV comprising administering to a human in need thereof a therapeutically effective quantity of a compound according to formula I, wherein $R^1$ to $R^7$ are as defined hereinabove.

In another embodiment of the present invention there is provided a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination with at least one immune system modulator and/or antiviral agent that inhibits replication of HCV.

In another embodiment of the present invention there is provided a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination with at least one immune system modulator.

In another embodiment of the present invention there is provided a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination with an interferon, interleukin, tumor necrosis factor, colony stimulating factor or an anti-inflammatory agent.

In another embodiment of the present invention there is provided a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination an interferon.

In another embodiment of the present invention is a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination with interferon-α or a chemically derivatized interferon.

In another embodiment of the present invention is a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination with at least one other antiviral agent.

In another embodiment of the present invention is a method for treating diseases mediated by HCV comprising administering to a mammal in need thereof a therapeutically effective quantity of a compound according to formula I, wherein $R^1$, $R^2$, $R^3$, $R^4$, $R^5$, $R^6$ and $R^7$ are as defined hereinabove, in combination with at least one HCV protease inhibitor, HCV polymerase inhibitor, HCV helicase inhibitor, HCV primase inhibitor, HCV integrase inhibitor or HCV fusion inhibitor.

In another embodiment of the present invention is a pharmaceutical composition comprising a therapeutically effective quantity of a compound of formula I, wherein $R^1$, $R^2$, $R^3$, $R^4$, $R^5$, $R^6$ and $R^7$ are as defined hereinabove, in combination with one or more pharmaceutically acceptable carrier, diluent or excipient with the proviso that at least one of $R^1$, $R^2$, $R^3$, or $R^4$ is other than hydrogen.

In another embodiment of the present invention there is provided a process for converting an N-acyl cytidine compound IVa to a cytidine compound IVb by selective cleavage of an N-acyl moiety from

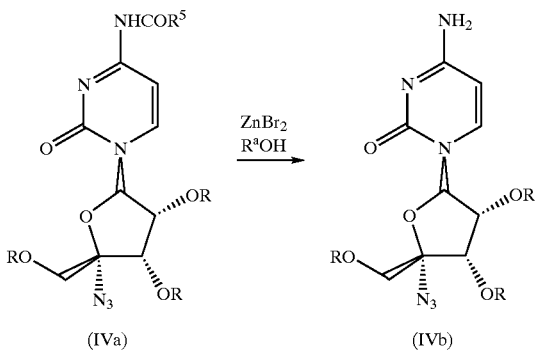

IVa wherein R is identical to $R^1$ as defined hereinabove; and $R^5$ $R^6$ and $R^7$ are as defined hereinabove, said process comprising contacting a solution of said N-acyl pyrimidine nucleoside with $ZnBr_2$ in a protic solvent $R^aOH$ wherein $R^a$ is hydrogen or $C_{1-4}$ alkyl.

In another embodiment of the present invention there is provided a process for converting IVa to IVb wherein R is identical to $R^1$ as defined hereinabove; and $R^5$ $R^6$ and $R^7$ are as defined hereinabove, said process comprising contacting a solution of said N-acyl pyrimidine nucleoside with $ZnBr_2$ in methanol and optimally with an aprotic organic solvent.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition for each group as provided in the Summary of the Invention.

The terms "optional" or "optionally" as used herein means that a described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

Compounds of the present invention may have asymmetric centers located on the side chain of a carboxylic ester, amide or carbonate moiety that produce diastereomers when linked to the nucleoside. All stereoisomers on the side chain of the compounds of the instant invention are contemplated, either in admixture or in pure or substantially pure form. The definition of the compounds according to the invention embraces all possible stereoisomers and their mixtures. It also embraces the racemic forms as well as the isolated optical isomers. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

All configurational isomers of compounds of the present invention are contemplated, either in admixture or in pure or substantially pure form. The definition of compounds of the present invention embraces both cis and trans isomers of cycloalkyl rings.

The term "alkyl" as used herein denotes an unbranched or branched chain hydrocarbon residue containing 1 to 18 carbon atoms. The term "lower alkyl" denotes an unbranched or branched chain hydrocarbon residue containing 1 to 6 carbon atoms. Representative lower alkyl groups include methyl, ethyl, propyl, i-propyl, n-butyl, i-butyl, t-butyl or pentyl.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "alkenyl" as used herein denotes an unsubstituted [or substituted] hydrocarbon chain radical having from 2 to 18 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes an unsubstituted hydrocarbon chain radical having from 2 to 18 carbon atoms, [preferably 2 to 4 carbon atoms], and having one or where possible two triple bonds[, preferably one triple bond]. Examples are ethynyl, 1-propynyl, 2-propynyl, 1-butynyl, 2-butynyl or 3-butynyl.

The term "alkoxy" as used herein denotes an unsubstituted unbranched or branched chain alkyloxy group wherein the "alkyl" portion is as defined above such as methoxy, ethoxy, n-propyloxy, i-propyloxy, n-butyloxy, i-butyloxy, t-butyloxy, pentyloxy, hexyloxy, heptyloxy including their isomers. "Lower alkoxy" as used herein denotes an alkoxy group with a "lower alkyl" group as previously defined.

The term "alkylthio" or "thioalkyl" as used herein denotes a unbranched or branched chain (alkyl)S-group wherein the "alkyl" portion is as defined above. Examples are methylthio, ethylthio, n-propylthio, i-propylthio, n-butylthio, i-butylthio or t-butylthio.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, and propyloxypentyl including their isomers.

The term "hydroxyalkyl" as used herein denotes a unbranched or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "aryl" as used herein denotes an optionally substituted monocyclic or polycyclic-aromatic group comprising carbon and hydrogen atoms. Examples of suitable aryl groups include, but are not limited to, phenyl and naphthyl (e. g. 1-naphthyl or 2-naphthyl). Suitable substituents for aryl are selected from the group consisting of alkyl, alkenyl, alkynyl, aryloxy, cycloalkyl, acyl, acylamino, alkoxy, amino, alkylamino, dialkylamino, halogen, haloalkyl, hydroxy, nitro and cyano.

The term "acyl" ("alkylcarbonyl") as used herein denotes a group of formula $C(=O)R$ wherein R is hydrogen, unbranched or branched alkyl containing 1 to 7 carbon atoms or a phenyl group.

The terms "alkoxycarbonyl" and "aryloxycarbonyl" as used herein denotes a group of formula $—C(=O)OR$ wherein R is alkyl or aryl respectively and alkyl and aryl are as defined herein.

The terms "thioalkylcarbonyl" and "arylthiocarbonyl" as used herein denotes a group of formula $—C(=O)SR$ wherein R is alkyl or aryl respectively and alkyl and aryl are as defined herein The term halogen stands for fluorine, chlorine, bromine or iodine, preferably fluorine, chlorine, bromine.

The term "amino acid" as used herein refers to naturally occurring amino acids, as well as to optical isomers (enantiomers and diastereomers), synthetic analogs and derivatives thereof. α-Amino acids comprise a carbon atom bonded to a carboxyl group, an amino group, a hydrogen atom and a unique "side chain" group. The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. The side chains of naturally occurring amino acids include: hydrogen, methyl, iso-propyl, iso-butyl, sec-butyl, $—CH_2OH$, $—CH(OH)CH_3$, $—CH_2SH$, $—CH_2CH_2SMe$, $—(CH_2)_pCOR$ wherein R is $—OH$ or $—NH_2$ and p is 1 or 2, $—(CH_2)_q—NH_2$ where q is 3 or 4, $—(CH_2)_3—NHC(=NH)NH_2$, $—CH_2C_6H_5$, $—CH_2$-p—$C_6H_4—OH$, (3-indolinyl)methylene, (4-imidazolyl)methylene.

The term "acylating agent" as used herein refers to either an anhydride, acyl halide or other activated derivative of a carboxylic acid. The term "anhydride" as used herein refers to compounds of the general structure $RC(O)—O—C(O)R$ wherein R is as defined in the previous paragraph. The term "acyl halide" as used herein refers to the group $RC(O)X$ wherein X is bromo or chloro. The term "activated derivative" of a compound as used herein refers to a transient reactive form of the original compound which renders the compound active in a desired chemical reaction, in which the original compound is only moderately reactive or nonreactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance. The term acylating agent as used herein further includes reagents that produce carbonates ($—OC(=O)OR^5$, carbamates ($—NHC(=O)OR^5$), thiocarbonate($—OC(=O)SR^5$), and thiocarbamate ($—NHC(=O)SR^5$), derivatives such as alkoxychlorocarbonates, $R^5OC(=O)Cl$, and alkylthiochlorocarbonates, $R^5SC(=O)Cl$, wherein $R^5$ is as defined hereinabove.

The term "protecting group" as used herein means a chemical group that (a) preserves a reactive group from participating in an undesirable chemical reaction; and (b) can be easily removed after protection of the reactive group is no longer required. For example, the trialkylsilyl is a protecting group for a primary hydroxyl function and an acetonide is a protecting group for a vicinal diol.

In the pictorial representation of the compounds given throughout this application, a thickened tapered line (◄■) indicates a substituent which is above the plane of the ring to which the asymmetric carbon belongs and a dotted line (••••ıııı) indicates a substituent which is below the plane of the ring to which the asymmetric carbon belongs.

The term "combination" as used herein in reference in administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1–3):217-24). A non-limiting list of chemically derivatized IFNα contemplated in the present patent include peginterferon-α-2a (PEGASYS®) and peginterferon-α-2b (PEGINTRON®).

Compounds of formula I exhibit tautomerism. Tautomeric compounds can exist as two or more interconvertable species. In many cases these entities result from the shift a covalently bonded hydrogen atom shift between two atoms. Tautomeric compounds exist in equilibrium with each other, so that attempts to isolate the individual tautomers usually produce a mixture having chemical and physical properties consistent with a mixture of compounds. The position of the equilibrium is dependent on chemical features within the molecule. For example, in many aliphatic aldehydes and ketones, such as acetaldehyde, the keto form predominates while; in phenols, the enol form predominates. The most common type of tautomerism is that involving carbonyl, (or keto) compounds and vinyl alcohols (or enols which arise from a hydrogen atom shift between the carbon and oxygen atoms and a concomitant shift in the position of the double bond. The present invention includes lactams which can exist as amide or hydroxy substituted heterocyclic forms.

Compounds of formula I which are basic can form pharmaceutically acceptable salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluene sulphonic acid, and the like). The formation and isolation of such salts can be carried out according to methods known in the art.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e,g., channels) that have a guest molecule (e,g.), a solvent or water) trapped within.

Compounds and Preparation

In general, the nomenclature used in this Application is based on AUTONOM™ v.4.0, a Beilstein Institute computerized system for the generation of IUPAC systematic nomenclature.

Examples of representative compounds within the scope of the invention are provided in the following table. These examples and preparations are provided to enable those skilled in the art to more clearly understand and to practice the present invention. They should not be considered as limiting the scope of the invention, but merely as being illustrative and representative thereof. The compounds of formula I may be prepared by various methods known in the art of organic chemistry.

TABLE 1

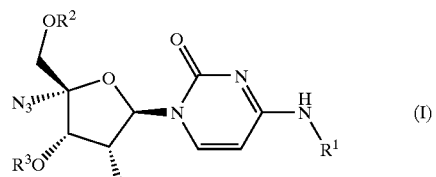

(I)

| Cpd No. | $R^1$ | $R^2$ | $R^3$ | $R^4$ | Method | Mass Spectrum (M + H)+ | Melting Point |
|---|---|---|---|---|---|---|---|
| 1 | MeCO | MeCO | MeCO | MeCO | A | 453 | 77.0–80.1 |
| 2 | EtCO | EtCO | EtCO | EtCO | A | 508(M)+ | |
| 3 | n-PrCO | n-PrCO | n-PrCO | n-PrCO | A | 564(M)+ | |
| 4 | i-BuCO | i-BuCO | i-BuCO | i-BuCO | A | 621 | |
| 5 | t-BuCO | t-BuCO | t-BuCO | t-BuCO | A | 621 | 67.4–80.0 |
| 6 | PhCO | PhCO | PhCO | PhCO | A | 700(M)+ | 106.9–116.1 |
| 7 | PhOCH$_2$CO | PhOCH$_2$CO | PhOCH$_2$CO | PhOCH$_2$CO | A | 821 | — |
| 8 | t-BuOCO | H | H | H | B | 385 | 80.0–83.5 |
| 9 | MeCO | H | H | H | B | 327 | 94.0–96.8 |
| 10 | EtCO | H | H | H | B | 341 | |
| 11 | n-PrCO | H | H | H | B | 355 | |
| 12 | i-PrCO | H | H | H | B | 355 | |
| 13 | t-BuCO | H | H | H | B | 369 | 108.0–114.0 |
| 14 | PhCO | H | H | H | B | 389 | 108.1–118.2 |
| 15 | PhCH$_2$CO | H | H | H | B | 403 | |

TABLE 1-continued

| Cpd No. | R¹ | R² | R³ | R⁴ | Method | Mass Spectrum (M + H)+ | Melting Point |
|---|---|---|---|---|---|---|---|
| 16 | PhOCH₂CO | H | H | H | B | 419 | |
| 17 | n-BuOCO | H | H | H | B | 385 | 86.5–94.0 |
| 18 | H | Val HCl | H | H | D | 384 | |
| 19 | H | Phe HCl | H | H | D | 432 | |
| 20 | H | Ala HCl | H | H | D | 356 | |
| 21 | H | PhCO | H | H | D | 389 | |
| 22 | H | MeCO | MeCO | MeCO | C | 411 | |
| 23 | H | EtCO | EtCO | EtCO | C | 453 | 75.9–79.9 |
| 24 | H | i-PrCO | i-PrCO | i-PrCO | C | 495 | |
| 25 | H | PhCO | PhCO | PhCO | C | | |
| 26 | H | PhCO | PhCO | 3-Cl—PhCO | C | | |
| 27 | n-BuOCO | PhCO | PhCO | PhCO | C | 697 | |
| 28 | PhCH₂CO | i-PrCO | H | H | E | 473 | |
| 29 | H | n-PrCO | | C(CH₃)₃ | D | 395 | |
| 30 | H | PhCO | | C(CH₃)₃ | D | 429 | |
| 31 | H | Boc-Phe | | C(CH₃)₃ | D | 572 | |
| 32 | H | i-PrCO | | C(CH₃)₃ | D | 395 | |
| 33 | H | H | | C(CH₃)₃ | — | 325 | 106.2–120.1 |
| 34 | i-PrCO | i-PrCO | | C(CH₃)₃ | E | 465 | |
| 35 | MeCO | MeCO | | C(CH₃)₃ | E | 409 | 105.0–109.9 |
| 36 | PhCO | PhCO | | C(CH₃)₃ | E | 533 | |
| 37 | MeOCO | MeOCO | MeOCO | MeOCO | A | 517 | |
| 38¹ | Val-NH-Boc | H | H | H | A | 484 | 120.2–121.3 |
| 39 | H | i-PrCO | H | H | D | 355 | |
| 40² | H | i-PrCO | H | H | D | 355 | |
| 41² | H | n-PrCO | n-PrCO | n-PrCO | C | 495 | 52.6–58.4 |
| 42 | C₈H₁₇OCO | H | H | H | B | 441 | |
| 43² | H | PhCO | H | H | D | 389 | 163–166.5 |
| 44 | C₇H₁₅OCO | H | H | H | B | 427 | |
| 45² | H | i-BuCO | i-BuCO | i-BuCO | C | 537 | 142–142.8 |
| 46² | H | n-BuCO | n-BuCO | n-BuCO | C | | 72.9–74.7 |
| 47 | C₆H₁₃OCO | H | H | H | B | 413 | 134.4–136.0 |
| 48 | H | H | i-PrCO | i-PrCO | F | 425 | |
| 49² | H | Ile HCl | H | H | D | 398 | |
| 50² | H | t-BuCO | t-BuCO | t-BuCO | F | | 136.2–140 |
| 51 | n-PrOCO | H | H | H | B | 371 | |
| 52 | n-C₅H₁₁OCO | H | H | H | B | 399 | |
| 53 | i-BuOCO | H | H | H | B | 385 | |
| 54² | H | MeCO | MeCO | MeCO | C | 411 | 88.0–90.9 |
| 55 | i-PrCO | i-PrCO | i-PrCO | i-PrCO | A | 565 | 60.4–64 |
| 56² | H | i-PrCO | i-PrCO | i-PrCO | A | | 145–146.9 |
| 57 | MeOCO | H | H | H | B | | 141.1–141.8 |
| 58 | EtOCO | H | H | H | B | 357 | |
| 59² | H | EtCO | EtCO | EtCO | C | | 72–75.2 |
| 60 | PhCO | EtCO | EtCO | EtCO | C⁴ | 557 | 54.6–56.9 |
| 61² | H | n-PrCO | H | H | D | 355 | |
| 62² | H | PhCO | PhCO | PhCO | D | 597 | 208.9–210.3 |
| 63² | H | n-C₅H₁₁CO | H | H | D | 383 | |
| 64³ | H | COOC₆H₁₃ | Hb | H | D | | 71.0–103.9 |
| 65³ | H | COOC₇H₁₅ | H | H | D | | 90.9–94.6 |
| 66³ | H | COOC₈H₁₃ | H | H | D | | 70.5–81 |
| 67² | H | n-C₇H₁₅CO | H | H | D | 411 | |
| 68² | H | Δ⁹-E n-C₁₈H₃₅CO | H | H | D | 549 | |
| 69 | COO-i-Pr | H | H | H | D | 371 | |
| 70² | H | n-C₅H₁₁CO | H | H | D | 397 | |
| 71² | H | n-C₁₁H₂₃CO | H | H | D | | 154–155 |
| 72 | H | n-C₁₀H₂₁CO | H | H | D | | 128–129.9 |
| 73² | H | n-C₉H₁₉CO | H | H | D | | 180.6–181.2 |
| 74 | H | n-C₁₃H₂₇CO | H | H | D | 495 | 116.8–128 |
| 75 | H | n-C₈H₁₉CO | H | H | D | | 96–100.4 |
| 76 | H | n-C₆H₁₃CO | H | H | D | | 55.3–56.5 |
| 77 | H | n-C₁₅H₃₁CO | H | H | D | 523 | 124–163.4 |
| 78 | H | Δ⁹-Z n-C₈H₁₇CO | H | H | D | | 172–172.3 |
| 79 | COO-n-Bu | CO-i-Bu | CO-i-Bu | CO-i-Bu | B/C⁶ | 637 | |
| 80 | COO-n-Bu | COEt | COEt | COEt | B/C⁶ | 553 | |

TABLE 1-continued

| Cpd No. | R¹ | R² | R³ | R⁴ | Method | Mass Spectrum (M + H)+ | Melting Point |
|---|---|---|---|---|---|---|---|
| 81[3] | H | H | CO-n-$C_5H_{11}$ | CO-n-$C_5H_{11}$ | F | 481 | |
| 82[3] | H | H | CO-n-Bu | CO-n-Bu | F | 453 | |
| 83[2] | H | H | CO-n-Bu | COn-Bu | F | | 124.3–128.4 |
| 84[2] | H | 4-methyl-benzoate | H | H | D | | 187–189 |
| 85[2] | H | CO-n-$C_{13}H_{27}$ | H | H | D | | 178.6–179.4 |
| 86[3] | H | COO-n-$C_{10}H_{21}$ | H | H | D | | 75–77.7 |
| 87 | H | CO-n-$C_{11}H_{23}$ | H | H | D | 467 | |
| 88[3] | H | H | CO-n-Pr | CO-n-Pr | F | | 91–94.9 |
| 89[2] | H | H | CO-n-Pr | CO-n-Pr | F | | 154.6–155.6 |
| 90[2] | H | COO-n-$C_9H_{19}$ | H | H | D | | 174.7–176.1 |
| 91[2] | H | H | CO-i-Pr | CO-i-Pr | F | | 191.1–191.9 |
| 92[2] | H | H | CO—Ph | CO—Ph | F | | 166.2–168.1 |
| 93[2] | H | H | CO—Et | CO—Et | F | | 194.6–198.2 |
| 94[2] | H | COO-n-Pr | COO-n-Pr | COO-n-Pr | C | | 167.5–170.6 |
| 95[5] | H | CO—Et | CO—Et | CO—Et | C | | 149–153 |
| 96 | COO-n-$C_5H_{11}$ | COO-n-$C_5H_{11}$ | H | H | E | | 56–57.5 |
| 97 | COO-n-$C_6H_{13}$ | COO-n-$C_6H_{13}$ | H | H | E | | |
| 98[2] | H | CONH-n-$C_8H_{13}$ | H | H | D | | 164.9–168.5 |
| 99 | CO-n-$C_5H_{11}$ | CO—Ph | H | H | E | 503 | 67.4–73.9 |
| 100 | CO-n-$C_6H_{13}$ | CO—Ph | H | H | E | 517 | 70.2–74.6 |
| 101[5] | H | H | CO-n-Bu | CO-n-Bu | F | | 115.3–120.1 |
| 105[2] | H | H | CO-n-$C_5H_{11}$ | CO-n-$C_5H_{11}$ | F | | 127.3–128.6 |
| 103[2] | H | CO-n-Bu | H | H | D | | 62.1–87.7 |

Val HCl = $Cl^{-+}NH_3CH(CHMe_2)CO$
Phe HCl = $Cl^{-+}NH_3CH(CH_2Ph)CO$
Ala HCl = $Cl^{-+}NH_3CH(Me)CO$
Ile HCl = $Cl^{-+}NH_3CH[CH(Me)Et]CO$
Val-NH-Boc = $Me_3COC(=O)NHCH(CHMe_2)CO$

[1] Prepared as described in Example 2 but substituting except the acid chloride was replace with Boc-Val-NCA (N-Carboxy Anhydride)
[2] hydrochloride salt
[3] trifluoroacetic acid salt These compounds also were available by N-boc protection of compound no. 34 followed by alkoxycarbonation of the hydroxymethyl substituent and deprotection with trifluoroacetic acid/$CH_2Cl_2$.
[4] Prepared by conversion of compound 59 to the free base and acylation with benzoyl chloride.
[5] Mesylate salt ($MeSO_3^-$)
[6] Prepared by initial N-acylation according to method B followed by O-acylation as in method C

TABLE 1-A

| Cpd No. | Chemical Name |
|---|---|
| 1 | Acetic acid (2R,3S,4R,5R)-3,4-diacetoxy-5-(4-acetylamino-2-oxo-2H-pyrimidin-1-yl)-2-azido-tetrahydro-furan-2-ylmethyl ester |
| 2 | Propionic acid (2R,3S,4R,5R)-2-azido-5-(2-oxo-4-propionylamino-2H-pyrimidin-1-yl)-3,4-bis-propionyloxy-tetrahydro-furan-2-ylmethyl ester |
| 3 | Butyric acid (2R,3S,4R,5R)-2-azido-5-(4-butyrylamino-2-oxo-2H-pyrimidin-1-yl)-3,4-bis-butyryloxy-tetrahydro-furan-2-ylmethyl ester |
| 4 | 3-Methyl-butyric acid (2R,3S,4R,5R)-2-azido-5-[4-(3-methyl-butyrylamino)-2-oxo-2H-pyrimidin-1-yl]-4-(3-methyl-butyryloxy)-2-(3-methyl-butyryloxymethyl)-tetrahydro-furan-3-yl ester |
| 5 | 2,2-Dimethyl-propionic acid (2R,3S,4R,5R)-2-azido-5-[4-(2,2-dimethyl-propionylamino)-2-oxo-2H-pyrimidin-1-yl]-3,4-bis-(2,2-dimethyl-propionyloxy)-tetrahydro-furan-2-ylmethyl ester |
| 6 | Benzoic acid (2R,3S,4R,5R)-2-azido-3,4-dibenzoyloxy-5-(4-benzoylamino-2-oxo-2H-pyrimidin-1-yl)-tetrahydro-furan-2-ylmethyl ester |
| 7 | Phenoxy-acetic acid (2R,3S,4R,5R)-2-azido-5-[2-oxo-4-(2-phenoxy-acetylamino)-2H-pyrimidin-1-yl]-3,4-bis-(2-phenoxy-acetoxy)-tetrahydro-furan-2-ylmethyl ester |
| 8 | [1-((2R,3R,4S,5R)-5-Azido-3,4-dihydroxy-5-hydroxymethyl-tetrahydro-furan-2-yl)-2-oxo-1,2-dihydro-pyrimidin-4-yl]-carbamic acid tert-butyl ester |
| 9 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-acetamide |
| 10 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-propionamide |

TABLE 1-A-continued

| Cpd No. | Chemical Name |
|---|---|
| 11 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-butyramide |
| 12 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-isobutyramide |
| 13 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-2,2-dimethyl-propionamide |
| 14 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-benzamide |
| 15 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-2-phenyl-acetamide |
| 16 | N-[1-((2R,3R,4S,5R)-5-Azido-3,4-dihydroxy-5-hydroxymethyl-tetrahydro-furan-2-yl)-2-oxo-1,2-dihydro-pyrimidin-4-yl]-2-phenoxy-acetamide |
| 17 | [1-((2R,3R,4S,5R)-5-Azido-3,4-dihydroxy-5-hydroxymethyl-tetrahydro-furan-2-yl)-2-oxo-1,2-dihydro-pyrimidin-4-yl]-carbamic acid butyl ester |
| 18 | 1-[(2R,3S,4R,5R)-5-(4-Amino-2-oxo-2H-pyrimidin-1-yl)-2-azido-3,4-dihydroxy-tetrahydro-furan-2-ylmethoxycarbonyl]-2-methyl-propyl-ammonium; chloride |
| 19 | 1-[(2R,3S,4R,5R)-5-(4-Amino-2-oxo-2H-pyrimidin-1-yl)-2-azido-3,4-dihydroxy-tetrahydro-furan-2-ylmethoxycarbonyl]-2-phenyl-ethyl-ammonium; chloride |
| 20 | 1-[(2R,3S,4R,5R)-5-(4-Amino-2-oxo-2H-pyrimidin-1-yl)-2-azido-3,4-dihydroxy-tetrahydro-furan-2-ylmethoxycarbonyl]-ethyl-ammonium; chloride |
| 21 | Benzoic acid (2R,3S,4R,5R)-5-(4-amino-2-oxo-2H-pyrimidin-1-yl)-2-azido-3,4-dihydroxy-tetrahydro-furan-2-y lmethyl ester |
| 22 | Acetic acid (2R,3S,4R,5R)-4-acetoxy-2-acetoxymethyl-5-(4-amino-2-oxo-2H-pyrimidin-1-yl)-2-azido-tetrahydro-furan-3-yl ester |
| 23 | Propionic acid (2R,3S,4R,5R)-5-(4-amino-2-oxo-2H-pyrimidin-1-yl)-2-azido-4-propionyloxy-2-propionyloxymethyl-tetrahydro-furan-3-yl ester |
| 24 | Isobutyric acid (2R,3S,4R,5R)-5-(4-amino-2-oxo-2H-pyrimidin-1-yl)-2-azido-4-isobutyryloxy-2-isobutyryloxymethyl-tetrahydro-furan-3-yl ester |
| 25 | Benzoic acid (2R,3S,4R,5R)-3,4-dibenzoyloxy-5-(4-amino-2-oxo-2H-pyrimidin-1-yl)-2-azido-tetrahydro-furan-2-ylmethyl ester |
| 26 | Benzoic acid (2R,3S,4R,5R)-3-(3-chloro-benzoyloxy)-4-benzoyloxy-5-(4-amino-2-oxo-2H-pyrimidin-1-yl)-2-azido-tetrahydro-furan-2-ylmethyl ester |
| 27 | Benzoic acid (2R,3S,4R,5R)-3,4-dibenzoyloxy-2-azido-5-(4-butoxycarbonylamino-2-oxo-2H-pyrimidin-1-yl)-tetrahydro-furan-2-ylmethyl ester |
| 28 | Isobutyric acid (2R,3S,4R,5R)-2-azido-3,4-dihydroxy-5-[2-oxo-4-(2-phenoxy-acetylamino)-2H-pyrimidin-1-yl]-tetrahydro-furan-2-ylmethyl ester |
| 29 | Butyric acid (3aS,4R,6R,6aR)-6-(4-amino-2-oxo-2H-pyrimidin-1-yl)-4-azido-2,2-dimethyl-tetrahydro-furo[3,4-d][1,3]dioxol-4-ylmethyl ester |
| 30 | Benzoic acid (3aS,4R,6R,6aR)-6-(4-amino-2-oxo-2H-pyrimidin-1-yl)-4-azido-2,2-dimethyl-tetrahydro-furo[3,4-d][1,3]dioxol-4-ylmethyl ester |
| 31 | 2-tert-Butoxycarbonylamino-3-phenyl-propionic acid (3aS,4R,6R,6aR)-6-(4-amino-2-oxo-2H-pyrimidin-1-yl)-4-azido-2,2-dimethyl-tetrahydro-furo[3,4-d][1,3]dioxol-4-ylmethyl ester |
| 32 | Isobutyric acid (3aS,4R,6R,6aR)-6-(4-amino-2-oxo-2H-pyrimidin-1-yl)-4-azido-2,2-dimethyl-tetrahydro-furo[3,4-d][1,3]dioxol-4-ylmethyl ester |
| 33 | 4-Amino-1-((3aR,4R,6R,6aS)-6-azido-6-hydroxymethyl-2,2-dimethyl-tetrahydro-furo[3,4-d][1,3]dioxol-4-yl)-1H-pyrimidin-2-one |
| 34 | Isobutyric acid (3aS,4R,6R,6aR)-4-azido-6-(4-isobutyrylamino-2-oxo-2H-pyrimidin-1-yl)-2,2-dimethyl-tetrahydro-furo[3,4-d][1,3]dioxol-4-ylmethyl ester |
| 35 | Acetic acid (3aS,4R,6R,6aR)-6-(4-acetylamino-2-oxo-2H-pyrimidin-1-yl)-4-azido-2,2-dimethyl-tetrahydro-furo[3,4-d][1,3]dioxol-4-ylmethyl ester |
| 36 | Benzoic acid (3aS,4R,6R,6aR)-4-azido-6-(4-benzoylamino-2-oxo-2H-pyrimidin-1-yl)-2,2-dimethyl-tetrahydro-furo[3,4-d][1,3]dioxol-4-ylmethyl ester |
| 37 | Carbonic acid (2R,3R,4S,5R)-5-azido-2-(4-butoxycarbonylamino-2-oxo-2H-pyrimidin-1-yl)-4-butoxycarbonyloxy-5-butoxycarbonyloxy-methyl-tetrahydro-furan-3-yl ester butyl ester |
| 38[1] | 1-[1-((2R,3R,4S,5R)-5-Azido-3,4-dihydroxy-5-hydroxymethyl-tetrahydro-furan-2-yl)-2-oxo-1,2-dihydro-pyrimidin-4-ylcarbamoyl]-2-methyl-propyl-ammonium; chloride |
| 39 | Isobutyric acid (2R,3S,4R)-5-((S)-4-amino-2-oxo-2H-pyrimidin-1-yl)-2-azido-3,4-dihydroxy-tetrahydro-furan-2-ylmethyl ester |
| 40[2] | (S)-1-((3R,4S,5R)-5-Azido-3,4-dihydroxy-5-isobutyryloxymethyl-tetrahydro-furan-2-yl)-2-oxo-1,2-dihydro-pyrimidin-4-yl-ammonium; chloride |
| 41[2] | (S)-1-((3R,4S,5R)-5-Azido-3,4-bis-isobutyryloxy-5-isobutyryloxymethyl-tetrahydro-furan-2-yl)-2-oxo-1,2-dihydro-pyrimidin-4-yl-ammonium; chloride |
| 42 | [(S)-1-((3R,4S,5R)-5-Azido-3,4-dihydroxy-5-hydroxymethyl-tetrahydro-furan-2-yl)-2-oxo-1,2-dihydro-pyrimidin-4-yl]-carbamic acid octyl ester |
| 43[2] | (S)-1-((3R,4S,5R)-5-Azido-5-benzoyloxymethyl-3,4-dihydroxy-tetrahydro-furan-2-yl)-2-oxo-1,2-dihydro-pyrimidin-4-yl-ammonium; chloride |
| 44 | [(S)-1-((3R,4S,5R)-5-Azido-3,4-dihydroxy-5-hydroxymethyl-tetrahydro-furan-2-yl)-2-oxo-1,2-dihydro-pyrimidin-4-yl]-carbamic acid heptyl ester |
| 45[2] | (S)-1-[(3R,4S,5R)-5-Azido-3,4-bis-(3-methyl-butyryloxy)-5-(3-methyl-butyryloxymethyl)-tetrahydro-furan-2-yl]-2-oxo-1,2-dihydro-pyrimidin-4-yl-ammonium; chloride |
| 46[2] | (S)-1-((3R,4S,5R)-5-Azido-3,4-bis-pentanoyloxy-5-pentanoyloxymethyl-tetrahydro-furan-2-yl)-2-oxo-1,2-dihydro-pyrimidin-4-yl-ammonium; chloride |
| 47 | [(S)-1-((3R,4S,5R)-5-Azido-3,4-dihydroxy-5-hydroxymethyl-tetrahydro-furan-2-yl)-2-oxo-1,2-dihydro-pyrimidin-4-yl]-carbamic acid hexyl ester |
| 48 | Isobutyric acid (2R,3S,4R,5R)-5-(4-amino-2-oxo-2H-pyrimidin-1-yl)-2-azido-2-hydroxymethyl-4-isobutyryloxy-tetrahydro-furan-3-yl ester |

TABLE 1-A-continued

| Cpd No. | Chemical Name |
|---|---|
| 49[2] | 1-[(2R,3S,4R)-5-((S)-4-Amino-2-oxo-2H-pyrimidin-1-yl)-2-azido-3,4-dihydroxy-tetrahydro-furan-2-ylmethoxycarbonyl]-2-methyl-butyl-ammonium; chloride |
| 50[2] | (S)-1-[(2R,3S,4R)-5-azido-3,4-bis-(2,2-dimethyl-propionyloxy)-5-(2,2-dimethyl-propionyloxymethyl)-tetrahydro-furan-2-yl)-2-oxo-1,2-dihydro-pyrimidin-4-yl-ammonium; chloride |
| 51 | Carbonic acid (2R,3S,4R)-5-((S)-4-amino-2-oxo-2H-pyrimidin-1-yl)-2-azido-3,4-dihydroxy-tetrahydro-furan-2-ylmethyl ester propyl ester |
| 52 | Carbonic acid (2R,3S,4R)-5-((S)-4-amino-2-oxo-2H-pyrimidin-1-yl)-2-azido-3,4-dihydroxy-tetrahydro-furan-2-ylmethyl ester pentyl ester |
| 53 | Carbonic acid (2R,3S,4R)-5-((S)-4-amino-2-oxo-2H-pyrimidin-1-yl)-2-azido-3,4-dihydroxy-tetrahydro-furan-2-ylmethyl ester isobutyl ester |
| 54[2] | (S)-1-((3R,4S,5R)-3,4-Diacetoxy-5-acetoxymethyl-5-azido-tetrahydro-furan-2-yl)-2-oxo-1,2-dihydro-pyrimidin-4-yl-ammonium; chloride |
| 55 | Isobutyric acid (2R,3S,4R)-2-azido-5-((S)-4-isobutyrylamino-2-oxo-2H-pyrimidin-1-yl)-4-isobutyryloxy-2-isobutyryloxymethyl-tetrahydro-furan-3-yl ester |
| 56[2] | (S)-1-((3R,4S,5R)-5-Azido-3,4-bis-isobutyryloxy-5-isobutyryloxymethyl-tetrahydro-furan-2-yl)-2-oxo-1,2-dihydro-pyrimidin-4-yl-ammonium; chloride |
| 57 | [(S)-1-((3R,4S,5R)-5-Azido-3,4-dihydroxy-5-hydroxymethyl-tetrahydro-furan-2-yl)-2-oxo-1,2-dihydro-pyrimidin-4-yl]-carbamic acid methyl ester |
| 58 | [(S)-1-((3R,4S,5R)-5-Azido-3,4-dihydroxy-5-hydroxymethyl-tetrahydro-furan-2-yl)-2-oxo-1,2-dihydro-pyrimidin-4-yl]-carbamic acid ethyl ester |
| 59[2] | (S)-1-((3R,4S,5R)-5-Azido-3,4-bis-propionyloxy-5-propionyloxymethyl-tetrahydro-furan-2-yl)-2-oxo-1,2-dihydro-pyrimidin-4-yl-ammonium; chloride |
| 60 | Propionic acid (2R,3S,4R)-2-azido-5-((S)-4-benzoylamino-2-oxo-2H-pyrimidin-1-yl)-4-propionyloxy-2-propionyloxymethyl-tetrahydro-furan-3-yl ester |
| 61[2] | (S)-1-((3R,4S,5R)-5-Azido-3,4-dihydroxy-5-propoxycarbonyloxymethyl-tetrahydro-furan-2-yl)-2-oxo-1,2-dihydro-pyrimidin-4-yl-ammonium; chloride |
| 62[2] | (S)-1-((3R,4S,5R)-5-Azido-3,4-bis-benzoyloxy-5-benzoyloxymethyl-tetrahydro-furan-2-yl)-2-oxo-1,2-dihydro-pyrimidin-4-yl-ammonium; chloride |
| 63[2] | (S)-1-((3R,4S,5R)-5-Azido-3,4-dihydroxy-5-pentyloxycarbonyloxymethyl-tetrahydro-furan-2-yl)-2-oxo-1,2-dihydro-pyrimidin-4-yl-ammonium; chloride |
| 64[3] | (S)-1-((3R,4S,5R)-5-Azido-3,4-dihydroxy-5-hexyloxycarbonyloxymethyl-tetrahydro-furan-2-yl)-2-oxo-1,2-dihydro-pyrimidin-4-yl-ammonium; trifluoro-acetate |
| 65[3] | (S)-1-((3R,4S,5R)-5-Azido-3,4-dihydroxy-5-heptyloxycarbonyloxymethyl-tetrahydro-furan-2-yl)-2-oxo-1,2-dihydro-pyrimidin-4-yl-ammonium; trifluoro-acetate |
| 66[3] | (S)-1-((3R,4S,5R)-5-Azido-3,4-dihydroxy-5-octyloxycarbonyloxymethyl-tetrahydro-furan-2-yl)-2-oxo-1,2-dihydro-pyrimidin-4-yl-ammonium; trifluoro-acetate |
| 67[2] | (S)-1-((3R,4S,5R)-5-Azido-3,4-dihydroxy-5-octanoyloxymethyl-tetrahydro-furan-2-yl)-oxo-1,2-dihydro-pyrimidin-4-yl-ammonium; chloride |
| 68[2] | (S)-1-[(3R,4S,5R)-5-Azido-3,4-dihydroxy-5-((E)-octadec-9-enoyloxymethyl)-tetrahydro-furan-2-yl]-2-oxo-1,2-dihydro-pyrimidin-4-yl-ammonium; chloride |
| 69 | [(S)-1-((3R,4S,5R)-5-Azido-3,4-dihydroxy-5-hydroxymethyl-tetrahydro-furan-2-yl)-2-oxo-1,2-dihydro-pyrimidin-4-yl]-carbamic acid isopropyl ester |
| 70[2] | (S)-1-((3R,4S,5R)-5-Azido-5-heptanoyloxymethyl-3,4-dihydroxy-tetrahydro-furan-2-yl)-2-oxo-1,2-dihydro-pyrimidin-4-yl-ammonium; chloride |
| 71[2] | (S)-1-((3R,4S,5R)-5-Azido-5-dodecanoyloxymethyl-3,4-dihydroxy-tetrahydro-furan-2-yl)-2-oxo-1,2-dihydro-pyrimidin-4-yl-ammonium; chloride |
| 72 | Undecanoic acid (2R,3S,4R)-5-((S)-4-amino-2-oxo-2H-pyrimidin-1-yl)-2-azido-3,4-dihydroxy-tetrahydro-furan-2-ylmethyl ester |
| 73[2] | (S)-1-((3R,4S,5R)-5-Azido-5-decanoyloxymethyl-3,4-dihydroxy-tetrahydro-furan-2-yl)-2-oxo-1,2-dihydro-pyrimidin-4-yl-ammonium; chloride |
| 74 | Tetradecanoic acid (2R,3S,4R)-5-((S)-4-amino-2-oxo-2H-pyrimidin-1-yl)-2-azido-3,4-dihydroxy-tetrahydro-furan-2-ylmethyl ester |
| 75 | Nonanoic acid ((2R,3S,4R)-5-((S)4-amino-2-oxo-2H-pyrimidin-1-yl)-2-azido-3,4-dihydroxy-tetrahydro-furan-2-ylmethyl ester |
| 76 | Heptanoic acid ((2R,3S,4R)-5-((S)4-amino-2-oxo-2H-pyrimidin-1-yl)-2-azido-3,4-dihydroxy-tetrahydro-furan-2-ylmethyl ester |
| 77 | Hexadecanoic acid (2R,3S,4R)-5-((S)-4-amino-2-oxo-2H-pyrimidin-1-yl)-2-azido-3,4-dihydroxy-tetrahydro-furan-2-ylmethyl ester |
| 78 | Z-Octadec-9-enoic acid (2R,3S,4R)-5-((S)4-amino-2-oxo-2H-pyrimidin-1-yl)-2-azido-3,4-dihydroxy-tetrahydro-furan-2-ylmethyl ester |
| 79 | 3-Methyl-butyric acid (2R,3S,4R)-2-azido-5-((S)-4-butoxycarbonylamino-2-oxo-2H-pyrimidin-1-yl)-3,4-bis-(3-methyl-butyryloxy)-tetrahydro-furan-2-ylmethyl ester |
| 80 | Propionic acid (2R,3S,4R)-2-azido-5-((S)-4-butoxycarbonylamino-2-oxo-2H-pyrimidin-1-yl)-3,4-bis-propionyloxy-tetrahydro-furan-2-ylmethyl ester |
| 81[3] | (S)-1-((3R,4S,5R)-5-Azido-3,4-bis-hexanoyloxy-5-hydroxymethyl-tetrahydro-furan-2-yl)-2-oxo-1,2-dihydro-pyrimidin-4-yl-ammonium; trifluoro-acetate |
| 82[3] | (S)-1-((3R,4S,5R)-5-azido-5-hydroxymethyl-3,4-bis-pentanoyloxy-tetrahydro-furan-2-yl)-2-oxo-1,2-dihydro-pyrimidin-4-yl-ammonium; trifluoro-acetate |
| 83[2] | (S)-1-((3R,4S,5R)-5-Azido-5-hydroxymethyl-3,4-bis-pentanoyloxy-tetrahydro-furan-2-yl)-2-oxo-1,2-dihydro-pyrimidin-4-yl-ammonium; chloride |
| 84[2] | (S)-1-[(3R,4S,5R)-5-Azido-3,4-dihydroxy-5-(4-methyl-benzoyloxymethyl)-tetrahydro-furan-2-yl]-2-oxo-1,2-dihydro-pyrimidin-4-yl-ammonium; chloride |
| 85[2] | (S)-1-((3R,4S,SR)-5-Azido-3,4-dihydroxy-5-tridecanoyloxymethyl-tetrahydro-furan-2-yl)-2-oxo-1,2-dihydro-pyrimidin-4-yl-ammonium; chloride |
| 86[3] | (S)-1-((3R,4S,5R)-5-Azido-5-decyloxycarbonyloxymethyl-3,4-dihydroxy-tetrahydro-furan-2-yl)-2-oxo-1,2-dihydro-pyrimidin-4-yl-ammonium; trifluoro-acetate |

TABLE 1-A-continued

| Cpd No. | Chemical Name |
|---|---|
| 87 | Dodecanoic acid (2R,3S,4R)-5-((S)-4-amino-2-oxo-2H-pyrimidin-1-yl)-2-azido-3,4-dihydroxy-tetrahydro-furan-2-ylmethyl ester |
| 88[3] | (S)-1-((3R,4S,5R)-5-azido-3,4-bis-butyryloxy-5-hydroxymethyl-tetrahydro-furan-2-yl)-2-oxo-1,2-dihydro-pyrimidin-4-yl-ammonium; trifluoro-acetate |
| 89[2] | (S)-1-((3R,4S,5R)-5-Azido-3,4-bis-butyryloxy-5-hydroxymethyl-tetrahydro-furan-2-yl)-2-oxo-1,2-dihydro-pyrimidin-4-yl-ammonium; chloride |
| 90[2] | (S)-1-((3R,4S,5R)-5-Azido-3,4-dihydroxy-5-nonyloxycarbonyloxymethyl-tetrahydro-furan-2-yl)-2-oxo-1,2-dihydro-pyrimidin-4-yl-ammonium; chloride |
| 91[2] | (S)-1-((3R,4S,5R)-5-Azido-5-hydroxymethyl-3,4-bis-isobutyryloxy-tetrahydro-furan-2-yl)-2-oxo-1,2-dihydro-pyrimidin-4-yl-ammonium; chloride |
| 92[2] | (S)-1-((3R,4S,5R)-5-Azido-3,4-bis-benzoyloxy-5-hydroxymethyl-tetrahydro-furan-2-yl)-2-oxo-1,2-dihydro-pyrimidin-4-yl-ammonium; chloride |
| 93[2] | (S)-1-((3R,4S,5R)-5-Azido-5-hydroxymethyl-3,4-bis-propionyloxy-tetrahydro-furan-2-yl)-2-oxo-1,2-dihydro-pyrimidin-4-yl-ammonium; chloride |
| 94[2] | (S)-1-((3R,4S,5R)-5-Azido-3,4-bis-butyryloxy-5-butyryloxymethyl-tetrahydro-furan-2-yl)-2-oxo-1,2-dihydro-pyrimidin-4-yl-ammonium; chloride |
| 95[2] | (S)-1-((3R,4S,5R)-5-azido-3,4-bis-propionyloxy-5-propionyloxymethyl-tetrahydro-furan-2-yl)-2-oxo-1,2-dihydro-pyrimidin-4-yl-ammonium; methanesulfonate |
| 96 | Carbonic acid (2R,3S,4R)-2-azido-3,4-dihydroxy-5-((S)-2-oxo-4-pentyloxycarbonylamino-2H-pyrimidin-1-yl)-tetrahydro-furan-2-ylmethyl ester pentyl ester |
| 97 | Carbonic acid (2R,3S,4R)-2-azido-5-((S)-4-hexyloxycarbonylamino-2-oxo-2H-pyrimidin-1-yl)-3,4-dihydroxy-tetrahydro-furan-2-ylmethyl ester hexyl ester |
| 98[2] | (S)-1-((3R,4S,5R)-5-Azido-3,4-dihydroxy-5-octylcarbamoyloxymethyl-tetrahydro-furan-2-yl)-2-oxo-1,2-dihydro-pyrimidin-4-yl-ammonium; chloride |
| 99 | Benzoic acid (2R,3S,4R)-2-azido-5-((S)-4-hexanoylamino-2-oxo-2H-pyrimidin-1-yl)-3,4-dihydroxy-tetrahydro-furan-2-ylmethyl ester |
| 100 | Benzoic acid (2R,3S,4R)-2-azido-5-((S)-4-heptanoylamino-2-oxo-2H-pyrimidin-1-yl)-3,4-dihydroxy-tetrahydro-furan-2-ylmethyl ester |
| 101[5] | (S)-1-((3R,4S,5R)-5-azido-5-hydroxymethyl-3,4-bis-pentanoyloxy-tetrahydro-furan-2-yl)-2-oxo-1,2-dihydro-pyrimidin-4-yl-ammonium; methanesulfonate |
| 102[2] | (S)-1-((3R,4S,5R)-5-azido-3,4-bis-hexanoyloxy-5-hydroxymethyl-tetrahydro-furan-2-yl)-2-oxo-1,2-dihydro-pyrimidin-4-yl-ammonium; methanesulfonate |
| 103[2] | (S)-1-((3R,4S,5R)-5-Azido-3,4-dihydroxy-5-pentanoyloxymethyl-tetrahydro-furan-2-yl)-2-oxo-1,2-dihydro-pyrimidin-4-yl-ammonium; chloride |

The compounds of formula I may be prepared by various methods known in the art of organic chemistry in general and nucleoside analogue synthesis in particular. Specific methodologies to prepare compounds of the present invention are illustrated in Examples 1–6. The starting materials for the syntheses are either readily available from commercial sources or are known or may themselves be prepared by techniques known in the art. General reviews of the preparation of nucleoside analogues are included in the following publications which are incorporated herein in their entirety:

A. M Michelson "The Chemistry of Nucleosides and Nucleotides", Academic Press, New York 1963.

L. Goodman "Basic Principles in Nucleic Acid Chemistry" Ed P O P Ts'O, Academic Press, New York 1974, Vol. 1, chapter 2.

"Synthetic Procedures in Nucleic acid Chemistry" Ed W W Zorbach and R S Tipson, Wiley, New York, 1973, Vol. 1 and 2.

H. Vorbrüggen and C. Ruh-Pohlenz (eds) "Handbook of Nucleoside Synthesis" Wiley, New York, 2001.

The compounds of the present invention are prepared by acylation of a suitable nucleoside compound. Acylation of alcohols (J. March, *Advanced Organic Chemistry* John Wiley & Sons, New York 1992 392–398; J. Mulzer *Synthesis of Esters, Activated Esters & Lactones in Comprehensive Organic Synthesis*, E. Winterfeldt, ed., vol. 6, Pergamon Press, Oxford 1991, pp.324–340) and amines (J. March, supra pp.417–425; H. G. Benz, *Synthesis of Amides and Related Compounds in Comprehensive Organic Synthesis*, E. Winterfeldt, ed., vol. 6, Pergamon Press, Oxford 1991 pp. 381–411) can be accomplished with a variety of acylating agents including acid chlorides and acid anhydrides. These references are incorporated herein in their entirety. Other methods for activation of a carboxylic acid have been developed and can be utilized to prepare the prodrugs described herein. The extent and pattern of acylation is controlled by use of suitable protecting groups or by the delaying the introduction of the basic amine into the pyrimidine base.

Tetraacyl nucleosides are readily prepared by acylating 1-((2R,3R,4S,5R)-5-azido-3,4-dihydroxy-5-hydroxymethyl-tetrahydro-furan-2-yl)-2-oxo-1,2-dihydro-pyrimidin-4-yl-ammonium; hydrogen sulfate (II) with at least 4 equivalents of acylating agent (Method A; Example 1).

Amines typically are more reactive toward acylating agents than are hydroxyl groups. Nonetheless to insure selective acylation of the amine substituent the hydroxyl groups are protected prior to acylation (Method B; Example 2). Trimethylsilyl ethers are useful protecting groups for this transformation.

More detailed information regarding protection and deprotection of alcohols and alternative protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 John Wiley and Sons, 1971–1996. The above references are incorporated herein by reference in their entirety.

Selective acylation of the three hydroxy substituents is accomplished by carrying out the acylation on the corresponding uridine nucleoside II, which lacks the reactive amine substituent on the heteroaromatic ring, and subsequently converting the uridine to a cytidine. The acylated uridine can be converted to cytidine by utilizing the method described by A. D. Borthwick et al., (*J. Med. Chem.* 1990, 33(1):179; see also K. J. Divakar and C. B. Reese *J. Chem Soc., Perkin Trans.* I 1982 1171–1176 and Maag et al. *J. Med. Chem.* 1992 35:1440–1451). The invention further provides a method for the selective cleavage of the N-acyl moiety from a N acylated nucleoside by contacting the N-acyl compound with zinc bromide in a protic solvent.

Selective acylation of the 5-hydroxy group and the amine was accomplished by protection of the vicinal 2',3'-hydroxy groups of a carbohydrate before acylation of the primary alcohol (Method E; Example 5). Protecting groups for vicinal diols often convert the diol into a dioxolane or dioxane ring (see Greene supra; Harrison and Harrison supra). Most commonly these protecting groups include aldehydes and ketones which readily form dioxolanes. Ketones which have found particular utility as diol protecting groups include acetone and $C_{5-7}$ cycloalkanones. Cleavage of the dioxolane or dioxane to regenerate the diol is generally accomplished with aqueous acid and an organic cosolvent. Benzaldehyde readily forms acetals with vic diols which can be deprotected by hydrogenolysis or acidic hydrolysis. Methoxy substitution on the benzaldehyde increases the rate of acidic hydrolysis and also permits cleavage of the dioxolane under oxidative conditions, e.g. $Ce(NH_4)_2(NO_3)_6$. Nitrobenzaldehydes afford dioxolanes which can be photochemically cleaved. Cyclic orthoesters, e.g. ethoxymethylene acetal have been utilized as diol protecting groups. These compounds can be cleaved under mild acidic conditions; however the initial product is an ester which must be hydrolyzed to regenerate the diol. The cyclic analog 2-oxacyclopentylidene orthoester affords the diol directly upon acid hydrolysis. Cyclic carbonates and cyclic boronates also have found some utility as diol protecting groups. Any of these diol protecting groups can be adapted to the present process.

5'-Monoacyl derivatives are accessible by protection of the 2',3' vicinal diol of a uridine derivative. Acylation of the remaining reactive hydroxyl is followed by conversion of the uridine base to the corresponding cytidine base as described above and deprotection of the vicinal diol (Method D; Example 4). Alternatively the N-acyl group of an N,1'-diacyl cytidine compound in which the 3' and 4' alcohols are protected can be selectively cleaved with zinc bromide to produce the protected monoacyl compound which can be further deprotected (R. Kierzek et al. *Tetrahedron Lett.* 1981 22(38): 3762–64).

Dosage and Administration

Compounds of the present invention may be administered either alone (i.e., monotherapy) or in combination with other therapeutic agents (e.g., "combination therapy"). Combination therapy can consist of an HCV polymerase inhibitor and immune modulators which stimulate natural immune responses to the virus and viral infected cells such as interferons, chemically modified interferons, interleukin, tumor necrosis factor or colony stimulating factors. Compounds of the present invention also can be combined with other antiviral compounds with a similar or complementary mode of action. Potential targets for antiviral drugs have been reviewed. (see e.g.,E. DeClercq, *Strategies in the Design of Antiviral Drugs, Nature Rev Drug Discov.* 2002 1(1):13–25; M. T. Reding, *Recent Developments in hepatitis C antiviral research 1999–2000, Exp Opin. Therap. Pat.* 2000, 10(8):1201–1220) Antiviral compounds including, but not limited to, HCV protease inhibitors, other HCV polymerase inhibitors, HCV helicase inhibitors, HCV primase inhibitors, HCV integrase inhibitors or HCV fusion inhibitors all could by useful in combination with compounds of the present invention.

The compounds of the present invention may be formulated in a wide variety of oral administration dosage forms and carriers. While nucleoside derivatives of the present invention are optimized for delivery across the gastrointestinal mucosa, these compounds can be efficacious when administered by other routes of administration. The pharmaceutically acceptable carriers may be either solid or liquid. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w).

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The term "preparation" or "dosage form" as used herein is intended to include the formulation of the active compound with encapsulating material as carrier, providing a capsule in which the active component, with or without carriers, is surrounded by a carrier, which is in association with it.

Similarly, cachets and lozenges are included. Tablets, powders, capsules, pills, cachets, and lozenges may be as solid forms suitable for oral administration.

Liquid formulations also are suitable for oral administration include liquid formulation including emulsions, syrups, elixirs, aqueous solutions, aqueous suspensions are also suitable forms for oral administration. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The phrase "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 0.7 g to 7.0 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions in Example 8 are given to enable those skilled in the art to more clearly understand and to practice the present invention. They should not be considered as limiting the scope of the invention, but merely as being illustrative and representative thereof.

The following preparations and examples are given to enable those skilled in the art to more clearly understand and to practice the present invention. They should not be considered as limiting the scope of the invention, but merely as being illustrative and representative thereof.

Efforts have been made to ensure accuracy with respect to numbers used (e.g., amounts, temperatures), but allowance for some experimental error and deviation, including differences in calibration, rounding of numbers, and the like, is contemplated.

EXAMPLE 1

Method A: Preparation of N, 2', 3', 4'-Tetraacyl Nucleoside Derivatives

Acetic acid 3,4-diacetoxy-5-(4-acetylamino-2-oxo-2H-pyrimidin-1-yl)-2-azido-tetrahydro-furan-2-ylmethyl ester

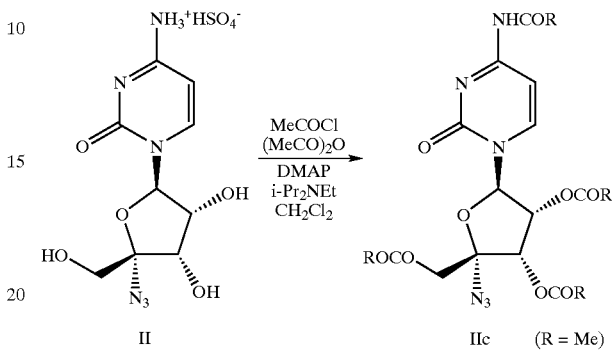

A stirred suspension of 4'-azidocytidine hemisulfate (0.30 g), dimethylaminopyridine (cat.), and N,N-diisopropylethylamine (3.69 mL) in methylene chloride (5 mL), under inert atmosphere, was cooled in an ice/water bath and treated dropwise with acetyl chloride (0.452 mL) and acetic anhydride (0.60 mL). The mixture was allowed to warm to ambient temperature and after 2 days was subjected, untreated, to flash chromatography (50% ethyl acetate in hexanes, then 75% ethyl acetate in hexanes, then 100% ethyl acetate, then 5% methanol in ethyl acetate) to afford 0.335 g of the solid product (compound 1; M+H=453

EXAMPLE 2

Method B: Preparation of N-acyl Nucleoside Derivatives

[1-(5-Azido-3,4-dihydroxy-5-hydroxymethyl-tetrahydro-furan-2-yl)-2-oxo-1,2-dihydro-pyrimidin-4-yl]-carbamic acid butyl ester

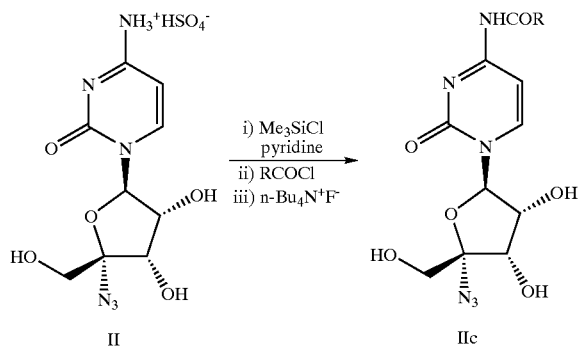

A stirred suspension of 4'-azidocytidine hemisulfate (0.50 g) in pyridine (8 mL), under inert atmosphere, was cooled in an ice/water bath and treated with trimethylsilyl chloride (1 mL). The mixture was allowed to warm to ambient temperature and after 1 h was treated with butyl chloroformate (0.2 mL). After stirring another 2 h at that temperature, the reaction was cooled in an ice/water bath and treated with 5 mL aqueous ammonium bicarbonate. The organics were extracted twice with methylene chloride, dried over magnesium sulfate, and filtered. To the filtrate was added tetra-n-butyl ammonium fluoride (0.25 mL, 1 M in tetrahydrofuran). The reaction was stirred at ambient temperature for three days. After solvent removal, the residue was subjected to flash chromatography (25% hexanes in ethyl acetate, then ethyl acetate, then 6.5% methanol in ethyl acetate) to afford 400 mg of the product as a solid (compound 17; mp 86.5–94° C.).

EXAMPLE 3

Method C: Preparation of 2', 3', 5'-Triacyl Nucleoside Derivatives

Acetic acid 3,4-diacetoxy-5-(4-amino-2-oxo-2H-pyrimidin-1-yl)-tetrahydro-furan-2-ylmethyl ester (22)

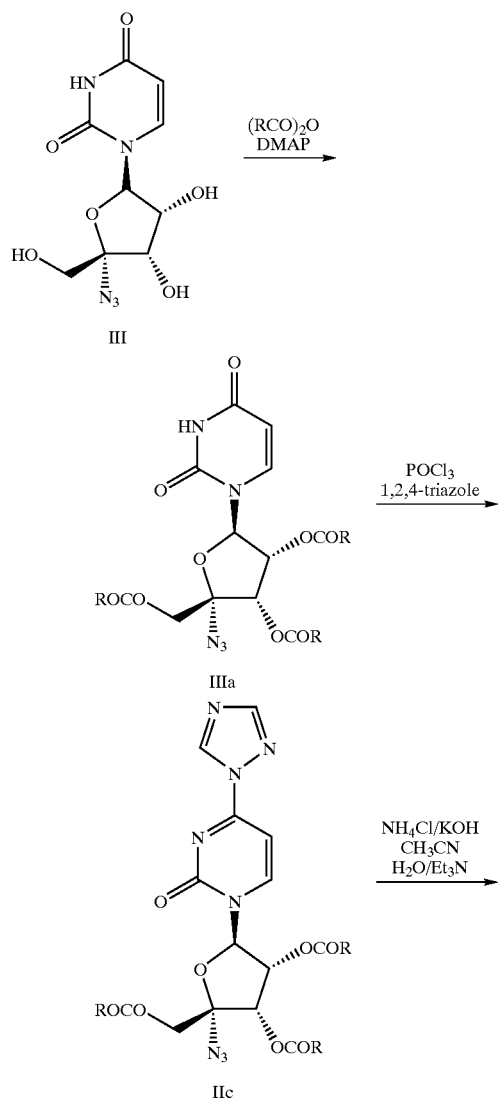

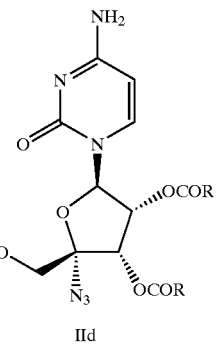

Step 1

To a stirred solution containing 0.330 g (1.15 mmol) 4'-azidouridine, 2 mL pyridine and 2 mL acetic anhydride was added 0.010 g (0.08 mmol) of 4-dimethylaminopyridine. After 12 h, the reaction mixture was evaporated to dryness under reduced pressure. The residue was dissolved in dichloromethane and washed with saturated aqueous sodium hydrogen carbonate solution, dried over magnesium sulfate and evaporated to dryness to give 0.42 g (88%) of 2',3',5'-tri-acetoxy-4'-azidouridine (IIIa: R=CH$_3$).

Step 2

POCl$_3$ (0.31 mL; 3.304 mmol) was added to a stirred mixture containing 0.340 g (0.826 mmol) of the uridine, 0.913 g (13.22 mmol) of 1,2,4-triazole and 2.30 mL (16.52 mmol) of triethylamine in 20 mL acetonitrile cooled to 5° C. The reaction mixture was allowed to warm to room temperature. After 12 h, the reaction mixture was evaporated to dryness under reduced pressure. The residue was diluted with dichloromethane, washed with saturated aqueous sodium hydrogen carbonate solution, dried over magnesium sulfate and evaporated to dryness to give 0.300 g (78%) of (IIc: R=CH$_3$).

Step 3

To a sealed flask containing 0.066 g (1.254 mmol) ammonium chloride and 0.070 g (1.254 mmol) of potassium hydroxide was added 10 mL acetonitrile, 20 mL water, 0.190 mL (1.278 mmol) of triethylamine followed by a solution containing 0.290 g (0.627 mmol) of the triazole in 10 mL acetonitrile. After 12 h, the mixture was evaporated to dryness under reduced pressure. The residue was dissolved in ethyl acetate and washed with water, dried over magnesium sulfate and evaporated to dryness under reduced pressure. Chromatography (10% methanol in dichloromethane) provided 0.060 g (23%) of the cytidine. (IId; R=CH$_3$; compound 22; MH$^+$=411; MNa$^+$=433).

Proceeding in similar fashion with the appropriate acylating agent there was obtained isobutyric acid 5-(4-amino-2-oxo-2H-pyrimidin-1-yl)-3,4-bis-isobutyryloxy-tetrahydro-furan-2-ylmethyl ester (compound 24; MH$^+$=495; MNa$^+$=517) and benzoic acid 5-(4-amino-2-oxo-2H-pyrimidin-1-yl)3,4-di-benzoxy-tetrahydro-furan-2-ylmethyl ester (compound 25).

EXAMPLE 4

Method D: Preparation of 5'-Acyl Nucleoside Derivatives

2-Amino-3-phenyl-propionic acid 5-(4-amino-2-oxo-2H-pyrimidin-1-yl)-3,4-dihydroxy-tetrahydro-furan-2-ylmethyl ester hydrochloride (Ie: R═CH(NH$_3^+$)CHC$_2$C$_6$H$_5$Cl; compound 19)

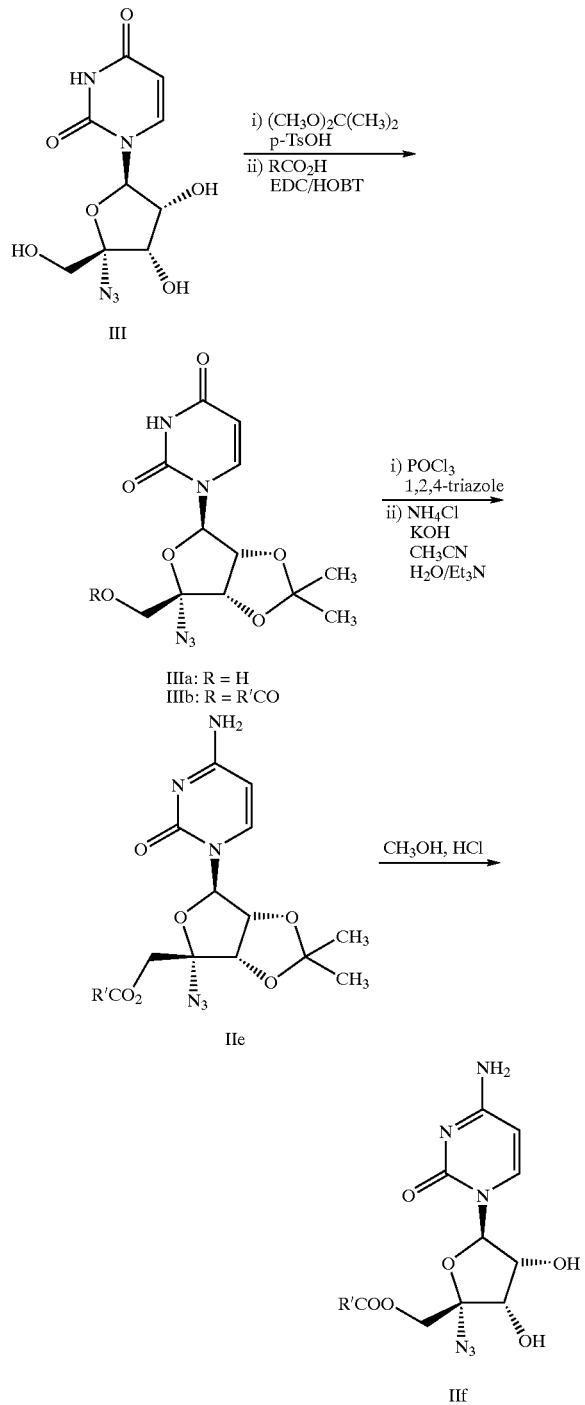

Step 1

1-(6-Hydroxymethyl-2,2-dimethyl-tetrahydro-furo[3,4-d][1,3]dioxol-4-yl)-1H-pyrimidine-2,4-dione (IIIb; compound 33)

A mixture containing 3.0 g (10.5 mmol) of 4'-azidouridine, 0.05 g (0.26 mmol) p-toluenesulfonic acid monohydrate and 6 mL (48.8 mmol) 2,2-dimethoxypropane in 20 mL acetone was stirred at room temperature for 12 h. The reaction mixture was diluted with ethyl acetate, washed with saturated aqueous sodium hydrogen carbonate solution, dried over magnesium sulfate and evaporated to dryness under reduced pressure to give the desired product 2.20 g (64%) of as a white solid.

Step 2

2-tert-Butoxycarbonylamino-3-phenyl-propionic acid 6-(2,4-dioxo-3,4-dihydro-2H-pyrimidin-1-yl)-2,2-dimethyl-tetrahydro-furo[3,4-d][1,3]dioxol-4-ylmethyl ester (IIIb: R═COCH(NH-boc)CH$_2$C$_6$H$_5$)

To a stirred solution containing 1.00 g (3.07 mmol) of 4'azido-2',3'-O-iso-propyl-uridine, 1.63 g (6.14 mmol) Boc-L-phenylalanine and 1.18 g (6.14 mmol) 1-(3-dimethylaminopropyl)-3-ethylcarbodimide hydrochloride in 20 mL N,N-dimethylformamide was added 0.375 g (3.07 mmol) of 4-dimethylaminopyridine. The resulting solution was left to stir under an atmosphere of nitrogen and at room temperature. After 12 h, the reaction mixture was evaporated to dryness under reduced pressure. Chromatography (0 to 100% ethyl acetate in hexanes) of the crude residue gave 1.01 g (57%) of the desired product as a white foam (MH$^+$=573; MNa$^+$=595).

Step 3

2-tert-Butoxycarbonylamino-3-phenyl-propionic acid 6-(4-amino-2-oxo-2H-pyrimidin-1-yl)-2,2-dimethyl-tetrahydro-furo[3,4-d][1,3]dioxol-4-ylmethyl ester (IIe: R═CH(NHboc)CH$_2$C$_6$H$_5$)

POCl$_3$ (0.651 mL; 6.98 mmol) was added to a stirred mixture containing 1.00 g (1.746 mmol) of the uridine, 1.93 g (27.94 mmol) of 1,2,4-triazole and 4.86 mL (34.93 mmol) of triethylamine in 50 mL acetonitrile cooled to 5° C. The reaction mixture was allowed to warm to room temperature. After 12 h, the reaction mixture was evaporated to dryness under reduced pressure. The residue was diluted with dichloromethane, washed with saturated aqueous sodium hydrogen carbonate solution, dried over magnesium sulfate and evaporated to dryness to give 1.0 g (92%) of the triazole.

To a sealed flask containing 0.171 g (3.207 mmol) ammonium chloride and 0.180 g (3.207 mmol) of potassium hydroxide was added 10 mL acetonitrile, 20 mL water, 0.446 mL (3.207 mmol) of triethylamine followed by a solution containing 1.00 g (1.603 mmol) of the phenylalanineuridine in 10 mL acetonitrile. After 12 h, the mixture was evaporated to dryness under reduced pressure. The residue was dissolved in ethyl acetate and washed with water, dried over magnesium sulfate and evaporated to dryness under reduced pressure. Chromatography (10% methanol in dichloromethane) provided 0.48 g (52%) of the cytidine. (MH$^+$=572; MNa$^+$=594).

Step 4:

2-Amino-3-phenyl-propionic acid 5-(4-amino-2-oxo-2H-pyrimidin-1-yl)-3,4-dihydroxy-tetrahydro-furan-2-ylmethyl ester hydrochloride (Ie: R═CH(NH$_3^+$)CH$_2$C$_6$H$_5$Cl$^-$)

To a solution containing 0.23 g (0.402 mmol) of phenylalanine cytidine (IIe: R═CH(NHBoc)CH$_2$Ph) in 10 mL of methanol was added 0.079 mL (0.804 mmol) concentrated hydrogen chloride solution. After 12 h, the reaction mixture was evaporated to dryness. The residue was dissolved in water and washed with ethyl acetate and evaporated to dryness under reduced pressure to give 0.160 g (94%) cytidine product (compound 19).

In similar fashion substituting boc-L-valine and boc-L-alanine there was obtained respectively, 2-amino-3-methyl-butyric acid 5-(4-amino-2-oxo-2H-pyrimidin-1-yl)-3,4-dihydroxy-tetrahydro-furan-2-ylmethyl ester hydrochloride (compound 18; MH$^+$=384; MNa$^+$=406) and 2-amino-propionic acid 5-(4-amino-2-oxo-2H-pyrimidin-1-yl)-3,4-dihydroxy-tetrahydro-furan-2-ylmethyl ester hydrochloride (compound 20; MH$^+$=356; MNa$^+$=378).

In similar manner utilizing benzoic anhydride there was obtained benzoic acid 5-(4-amino-2-oxo-2H-pyrimidin-1-yl)-3,4-dihydroxy-tetrahydro-furan-2-ylmethyl ester (compound 14; MH$^+$=389; MNa$^+$=411).

EXAMPLE 5

Method E

Isobutyric acid 2-azido-3,4-dihydroxy-5-(2-oxo-4-phenylacetylamino-2H-pyrimidin-1-yl)-tetrahydro-furan-2-ylmethyl ester

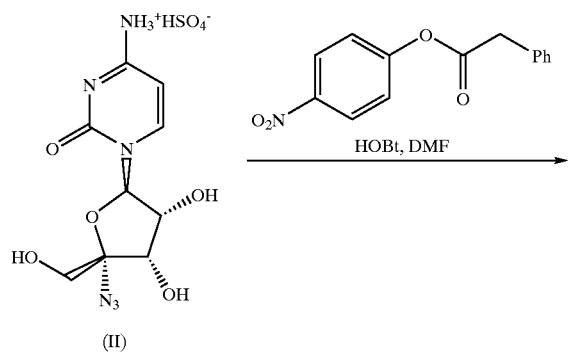

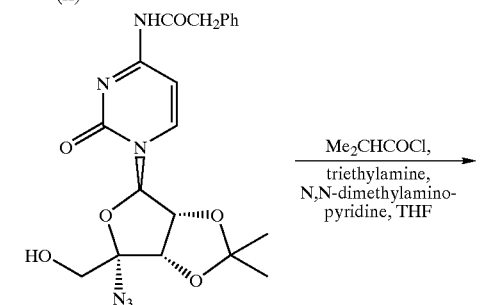

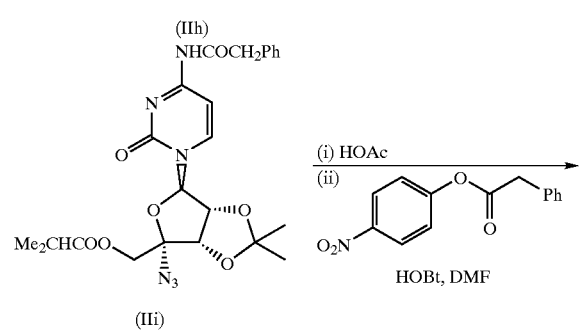

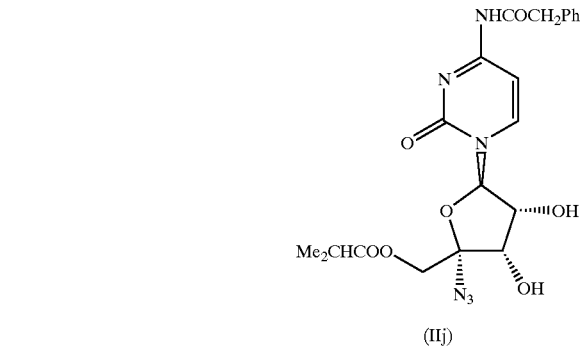

Step 1

A solution of 4-amino-1-(6-azido-6-hydroxymethyl-2,2-dimethyl-tetrahydro-furo[3,4-d][1,3]dioxol-4-yl)-1H-pyrimidin-2-one (II, 0.14 g), 4-nitrophenyl phenylacetate (0.12 g) and 1-hydroxybenzotriazole (0.06 g) in DMF (15 mL) was stirred at room temperature overnight. Water (15 mL) was added and the mixture was twice extracted with ethyl acetate. The combined ethyl acetate extracts were washed with water and brine and dried over anhydrous magnesium sulfate. The solution was concentrated in vacuo and purified by flash column chromatography which yielded IIh (0.18 g) as a colorless oil.

Step 2

IIh from the previous step (0.18 g), triethylamine (0.07 ml) and dimethylaminopyridine (0.01 g) were dissolved in THF (15 ml) and stirred at room temperature under nitrogen atmosphere. Isobutyroyl chloride (0.043 mL) was added slowly and the reaction was stirred at rt for 6 hours. Water (15 mL) was added and the mixture was extracted twice with ethyl acetate. The combined extracts were dried over anhydrous magnesium sulfate, filtered, and the solution concentrated in vacuo. The product (IIi; 0.18 g) was separated by a flash column chromatography as an oil.

Step 3

IIi (0.18 g) was dissolved in acetic acid (60%) and stirred at 100° C. overnight. The reaction was cooled to rt and the solvent evaporated under reduced pressure. The product was purified by preparatory thin layer chromatography. The crude product (69 mg) was dissolved in THF (10 ml) and treated at room temperature with 4-nitrophenyl phenylacetate (55 mg) and 1-hydroxybenzotriazole (26 mg). The reaction mixture was stirred at rt overnight. The solvent was evaporated and the residue was re-purified by preparatory thin layer chromatography to afford IIj (17 mg) as a colorless oil.

EXAMPLE 6

Method F

Isobutyric acid (2R,3S,4R,5R)-5-(4-amino-2-oxo-2H-pyrimidin-1-yl)-2-azido-2-hydroxymethyl-4-isobutyryloxy-tetrahydro-furan-3-yl ester

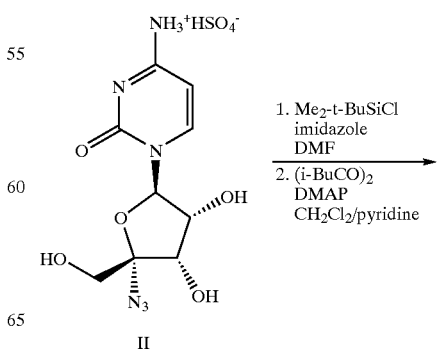

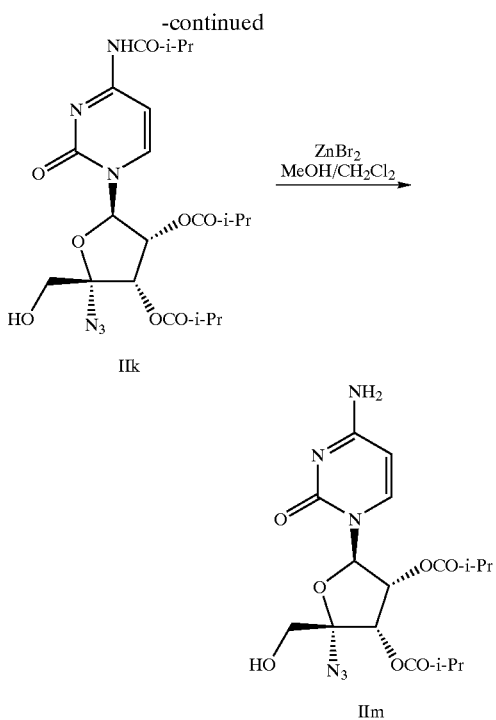

Step 1

A flask was charged with II (0.610 g; 1.75 mmol), dimethyl-tert-butylsilane (0.580 g; 3.84 mmol), imidazole (0.262 g; 3.842 mmol) and DMF (12 mL) and the resulting homogenous solution was stirred overnight at rt. Mass spectroscopy indicated the crude product was a mixture of mono- and disilylated product. The solvent was removed in vacuo and the residue was dissolved in pyridine (12 mL) and $CH_2Cl_2$ (12 mL) and a small catalytic quantity of DMAP and isobutyric anhydride (0.96 mL; 5.76 mmol) was added and the resulting mixture was stirred overnight at rt. The reaction mixture was extracted with a mixture of water and saturated $NaHCO_3$ and the aqueous layer back-extracted $CH_2Cl_2$. The organic layers were combined and extracted with IN HCl and water, dried ($MgSO_4$), filtered and evaporated to yield 1.3 g of crude silylated nucleosides as a yellow oil.

Step 2

The crude product (1.3 g) from the previous step was dissolved in THF (20 mL) and tetrabutyl ammonium fluoride (0.5 mL; TBAF; 1.0M solution in THF) was added and the reaction mixture was allowed to stir overnight. After 16 h, another 0.5 mL aliquot of TBAF was added and stirring continued for another 4 h and the solvent was evaporated. The residue was partitioned between $CH_2Cl_2$ and a mixture of $H_2O$ and saturated $NaHCO_3$. The aqueous extract was washed with $CH_2Cl_2$ and the combined organic extracts were washed with $H_2O$ and aqueous NaCl, dried, filtered and evaporated. The crude product was purified by flash chromatography and eluted with a gradient ($CH_2Cl_2 \rightarrow 4\%$ MeOH/$CH_2Cl_2$) to yield a colorless white solid N, 2',3'-tri-isobutyrate (IIk; 140 mg)

Step 3

The tri-isobutyrate (140 mg; 0.283 mmol) was dissolve in 2.5 mL $CH_2Cl_2$ and 0.8 mL of MeOH. To the resulting solution was added $ZnBr_2$ (6 mg; 0.283 mmol) and the resulting solution was stirred at 65° C. overnight. The solvent was removed in vacuo to yield 150 mg of a yellow foam which was purified by flash chromatography on silica gel and eluted with a gradient ($CH_2Cl_2 \rightarrow 75\%$ MeOH/$CH_2Cl_2$) to yield IIm (R=i-Pr) as a white solid (0.120 g; 98% theory).

EXAMPLE 7

Plasma Pharmacokinectics

Pharmacokinetic procedures were used to determine plasma levels of 4-amino-1-((2R,3R,4S,5R)-5-azido-3,4-dihydroxy-5-hydroxymethyl-tetrahydro-furan-2-yl)-1H-pyrimidin-2-one (II) after administration of a single oral 5 mg/kg dose of a prodrug of II. The formulation is a solution/suspension containing 0.0176 mmol of prodrug in 5 mL of an appropriate vehicle.

Three unfasted male Cynomolgus monkeys (6–9 kg) were fitted with a saphenous or brachial catheter to facilitate blood draw. Free access to food and water will be allowed at all times during the study. On the day of the study a predose blood sample (2–3 mL) was taken from each monkey. The monkeys were dosed with 1 mL/kg of the dose solution by oral gavage. At each of the following time points (0.25, 0.5, 1, 3, 5, 7, 10, 24, 32, and 48 hour) after dosing, approximately 0.5 mL of blood will be collected into lithium heparin-coated tubes. Blood was centrifuged to obtain plasma which was frozen until analysis.

The concentration of Ia ($R^1$—$R^4$=H) in each plasma sample was determined by an LC-MS assay. Standard curves were prepared in blank monkey plasma. The AUC represents the area under a plot of concentration vs time total which describes the concentration of the drug in systemic circulation as a function of time(L. Z. Benet, D. L. Kroetz and L. B. Sheiner *Pharmacokinetics in Goodman & Gilman's The Pharmacological Basis of Therapeutics*, J. G. Hardman & L. E. Limbird Eds., 9th Edition, McGraw Hill, New York, p 17–23). Cmax is the peak concentration which is found.

| Cpd No. | $AUC_{0-24h}$ (µg · h/mL) | AUC fold increase | Cmax (µg/mL) | Cmax fold increase |
|---|---|---|---|---|
| II | 2.85 | 1.00 | 0.312 | 1.00 |
| 24 | 10.5 | 3.83 | 1.42 | 4.55 |
| 46 | 12.01 | 4.23 | 2.21 | 6.33 |
| 82 | 12.96 | 4.56 | 1.73 | 4.96 |
| 86 | 10.41 | 9.67 | 1.69 | 4.84 |

EXAMPLE 7

Renilla Luciferase Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla*. luciferase gene was introduced into the first open reading frame of a replicon construct NK5.1 (Krieger et al., *J. Virol.* 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928–933). After in vitro transcription the RNA was electroporated into human hepatoma Huh7 cells, and G418-resistant colonies were isolated and expanded. Stably selected cell line 2209-23 contain replicative HCV subgenomic RNA, and the activity of *Renilla* luciferase expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation.

*Renilla* luciferase HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using Dual-Luciferase reporter assay system (Promega cat no. E1960) All the reagents described in the following paragraph were included in the manufacturers kit, and the manufacturer's instructions were followed for preparations of the reagents. The cells were washed twice with 200 μl of phosphate buffered saline (pH 7.0) (PBS) per well and lysed with 25 μl of 1× passive lysis buffer prior to incubation at room temperature for 20 min. One hundred microliter of LAR II reagent was added to each well. The plate was then inserted into the LB 96V microplate luminometer (MicroLumatPlus, Berthold), and 100 μl of Stop & Glo® reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microliter of WST-1 reagent was added to each well including wells that contain media alone as blanks. Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

| Compound Number | Luciferase Activity $IC_{50}$ (μM) |
| --- | --- |
| 5 | 5.33 |
| 18 | 2.4 |
| 25 | 2.47 |

EXAMPLE 8

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, with reference to the specific embodiments for purposes of clarity and understanding. It will be obvious to one of skill in the art that changes and modifications may be made and equivalents substituted without departing from the true spirit and scope of the invention. Therefore, it is to be understood that the above description is intended to be illustrative and not restrictive. Many modifications may be made to adapt a particular situation, material, composition of matter, process, or process step or steps, to the objective spirit and scope of the present invention. All such modifications are intended to be within the scope of the claims appended hereto All patents, patent applications and publications cited in this application are hereby incorporated by reference in their entirety for all purposes to the same extent as if each individual patent, patent application or publication were so individually denoted.

We claim:

1. A compound of formula I

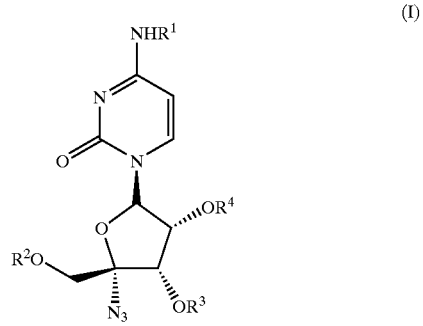

(I)

wherein:

$R^1$ and $R^2$ are independently selected from the group consisting of hydrogen, $COR^5$, $C(=O)OR^5$, $C(=O)SR^5$, $C(=O)NHR^5$ and $COCH(R^6)NHR^7$;

$R^3$ and $R^4$ are independently selected from the group consisting of hydrogen $COR^5$, $C(=O)OR^5$, $C(=O)SR^5$ and $COCH(R^6)NHR^7$; or, $R^3$ and $R^4$ taken together are selected from the group consisting of $CH_2$, $C(CH_3)_2$ and CHPh;

$R^5$ is independently selected from the group consisting of $C_{1-18}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, alkyl substituted $C_{3-8}$ cycloalkyl phenyl, phenyl optionally substituted with one to three substituents independently selected from the group consisting of halo, lower alkyl, lower alkoxy, lower thioalkyl, lower alkyl sulfinyl, lower alkyl sulfonyl, nitro, cyano, $CH_2Ph$ wherein in phenyl ring is optionally substituted as described above, and $CH_2OPh$ wherein in phenyl ring is optionally substituted as described above;

$R^6$ is independently selected from the group consisting of the side chains of naturally occurring amino acids and $C_{1-5}$ unbranched or branched alkyl;

$R^7$ is selected from the group consisting of hydrogen, $R^5OCO$; or, $R^6$ and $R^7$ taken together are $(CH_2)_3$; and, hydrates, solvates, clathrates and acid addition salts thereof; with the proviso that at least one of $R^1$, $R^2$, $R^3$, or $R^4$ is other than hydrogen.

2. A compound according to claim 1 wherein $R^1$, $R^2$, $R^3$, and $R^4$ each are independently $COR^5$, $C(=O)OR^5$, $C(=O)SR^5$ and each $R^5$ is independently selected from the group consisting of $C_{1-18}$ unbranched or branched lower alkyl, phenyl and $CH_2OPh$.

3. A compound according to claim 2 wherein $R^1$, $R^2$, $R^3$, and $R^4$ are $COR^5$ and each $R^5$ is independently selected from the group consisting of $C_{1-18}$ unbranched or branched lower alkyl, phenyl and $CH_2OPh$.

4. A compound according to claim 1 wherein $R^1$ is $COR^5$, $C(=O)OR^5$, $C(=O)SR^5$ or $COCH(R^6)NHR^7$ and $R^2$, $R^3$ and $R^4$ are hydrogen.

5. A compound according to claim 4 wherein $R^5$ is selected from a group consisting of $C_{1-18}$ unbranched or branched lower alkyl, $C_{3-8}$ cycloalkyl, phenyl and $CH_2OPh$, or $R^6$ is selected from the group consisting of $C_{1-5}$ unbranched or branched alkyl and the side chain of a naturally occurring amino acid.

6. A compound according to claim 1 wherein $R^2$ is selected from the group consisting of $COR^5$, $C(=O)OR^5$, $C(=O)SR^5$, and $COCH(R^6)NHR^7$, $R^1$, $R^3$ and $R^4$ are hydrogen.

7. A compound according to claim 6 wherein $R^5$ is selected from the group consisting of is $C_{1-18}$ unbranched or branched alkyl, $C_{3-8}$ cycloalkyl and phenyl or $R^6$ is $C_{1-5}$ unbranched or branched alkyl or the side chain of a naturally occurring amino acid.

8. A compound according to claim 6 wherein $R^2$ is $COCH(R^6)NH_2$ and $R^6$ is selected from the group consisting of $C_{1-5}$ unbranched or branched alkyl and $CH_2Ph$.

9. A compound according to claim 1 wherein $R^3$ and $R^4$ both are hydrogen.

10. A compound according to claim 1 wherein $R^1$ is hydrogen and $R^2$, $R^3$ and $R^4$ are independently selected from the group consisting of $COR^5$, $C(=O)OR^5$ and $C(=O)SR^5$.

11. A compound according to claim 1 wherein $R^1$ is hydrogen, $R^2$ is selected from the group consisting of $COR^5$, $C(=O)OR^5$, $C(=O)SR^5$ and $COCH(R^6)NHR^7$, and $R^3$ and $R^4$ taken together are selected from the group consisting of $CH_2$, $C(CH_3)_2$ and CHPh.

12. A compound according to claim 1 wherein $R^1$ and $R^2$ are hydrogen and $R^3$ and $R^4$ are independently selected from the group consisting of $COR^5$, $C(=O)OR^5$, $C(=O)SR^5$ and $COCH(R^6)NHR^7$ wherein $R^7$ is hydrogen.

13. A compound according to claim 1 wherein $R^1$ and $R^2$ are independently selected from the group consisting of $COR^5$, $C(=O)OR^5$, $C(=O)SR^5$ and $COCH(R^6)NHR^7$, and $R^3$ and $R^4$ taken together are selected from the group consisting of $CH_2$, $C(CH_3)_2$ and CHPh.

14. A compound according to claim 1 selected from the group consisting of:

Isobutyric acid (2R,3S,4R,5R)-5-(4-amino-2-oxo-2H-pyrimidin-1-yl)-2-azido-4-isobutyryloxy-2-isobutyryloxymethyl-tetrahydro-furan-3-yl ester;

(S)-1-((3R,4S,5R)-5-Azido-3,4-bis-propionyloxy-5-propionyloxymethyl-tetrahydro-furan-2-yl)-2-oxo-1,2-dihydro-pyrimidin-4-yl-ammonium; chloride;

(S)-1-((3R,4S,5R)-5-Azido-3,4-bis-pentanoyloxy-5-pentanoyloxymethyl-tetrahydro-furan-2-yl)-2-oxo-1,2-dihydro-pyrimidin-4-yl-ammonium; chloride;

(S)-1-[(3R,4S,5R)-5-Azido-3,4-dihydroxy-5-(4-methyl-benzoyloxymethyl)-tetrahydro-furan-2-yl]-2-oxo-1,2-dihydro-pyrimidin-4-yl-ammonium; chloride;

(S)-1-((3R,4S,5R)-5-azido-3,4-bis-hexanoyloxy-5-hydroxymethyl-tetrahydro-furan-2-yl)-2-oxo-1,2-dihydro-pyrimidin-4-yl-ammonium; methanesulfonate;

(S)-1-((3R,4S,5R)-5-azido-5-hydroxymethyl-3,4-bis-pentanoyloxy-tetrahydro-furan-2-yl)-2-oxo-1,2-dihydro-pyrimidin-4-yl-ammonium; trifluoro-acetate;

Tetradecanoic acid (2R,3S,4R)-5-((S)-4-amino-2-oxo-2H-pyrimidin-1-yl)-2-azido-3-dihydroxy-tetrahydro-furan-2-ylmethyl ester;

(S)-1-((3R,4S,5R)-5-azido-3,4-bis-butyryloxy-5-hydroxymethyl-tetrahydro-furan-2-yl)-2-oxo-1,2-dihydro-pyrimidin-4-yl-ammonium; trifluoro-acetate; and, (S)-1-((3R,4S,5R)-5-Azido-5-decyloxycarbonyloxymethyl-3,4-dihydroxy-tetrahydro-furan-2-yl)-2-oxo-1,2-dihydro-pyrimidin-4-yl-ammonium; trifluoro-acetate.

15. A method for treating a disease caused by the Hepatitis C Virus (HCV) comprising administering to a mammal in need thereof, a therapeutically effective quantity of a compound of formula I

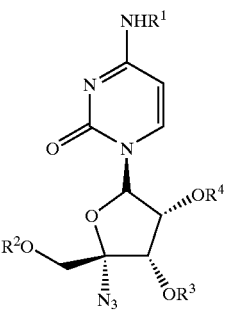

(I)

wherein:
$R^1$ and $R^2$ are independently selected from the group consisting of hydrogen, $COR^5$, $C(=O)OR^5$, $C(=O)SR^5$, $C(=O)NHR^5$ and $COCH(R^6)NHR^7$;

$R^3$ and $R^4$ are independently selected from the group consisting of hydrogen, $COR^5$, $C(=O)OR^5$, $C(=O)SR^5$ and $COCH(R^6)NHR^7$; or, $R^3$ and $R^4$ taken together are selected from the group consisting of $CH_2$, $C(CH_3)_2$ and CHPh;

$R^5$ is independently selected from the group consisting of $C_{1-18}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, alkyl substituted $C_{3-8}$ cycloalkyl phenyl, phenyl optionally substituted with one to three substituents independently selected from the group consisting of halo, lower alkyl, lower alkoxy, lower thioalkyl, lower alkyl sulfinyl, lower alkyl sulfonyl, nitro, cyano, $CH_2Ph$ wherein in phenyl ring is optionally substituted as described above, and $CH_2OPh$ wherein in phenyl ring is optionally substituted as described above;

$R^6$ is independently selected from the group consisting of the side chains of naturally occurring amino acids and $C_{1-5}$ unbranched or branched alkyl;

$R^7$ is selected from the group consisting of hydrogen, $R^5OCO$; or, $R^6$ and $R^7$ taken together are $(CH_2)_3$; and, hydrates, solvates, clathrates and acid addition salts thereof; with the proviso that at least one of $R^1$, $R^2$, $R^3$, or $R^4$ is other than hydrogen.

16. The method of claim 15 wherein $R^1$, $R^2$, $R^3$, and $R^4$ are each independently $COR^5$, $C(=O)OR^5$, $C(=O)SR^5$ and $R^5$ is independently selected from the group consisting of $C_{1-18}$ unbranched or branched lower alkyl, $C_{3-8}$ cycloalkyl, phenyl and $CH_2OPh$.

17. The method of claim 16 wherein $R^1$, $R^2$, $R^3$, and $R^4$ are each independently $COR^5$ and $R^5$ is independently selected from the group consisting of $C_{1-18}$ unbranched or branched lower alkyl, $C_{3-8}$ cycloalkyl, phenyl and $CH_2OPh$.

18. The method of claim 15 wherein $R^1$ is $COR^5$, $C(=O)OR^5$, $C(=O)SR^5$ or $COCH(R^6)NHR^7$ and $R^2$, $R^3$ and $R^4$ are hydrogen.

19. The method of claim 18 wherein $R^5$ is selected from a group consisting of $C_{1-18}$ unbranched or branched lower alkyl, $C_{3-8}$ cycloalkyl, phenyl and $CH_2OPh$, or $R^6$ is selected from the group consisting of $C_{1-5}$ unbranched or branched alkyl and the side chain of a naturally occurring amino acid and $R^7$ is hydrogen.

20. The method of claim 15 wherein $R^2$ is selected from the group consisting of $COR^5$, $C(=O)OR^5$, $C(=O)SR^5$, and $COCH(R^6)NHR^7$, $R^1$, $R^3$ and $R^4$ are hydrogen.

21. The method of claim 20 wherein $R^5$ is selected from the group consisting of is $C_{1-18}$ unbranched or branched alkyl, $C_{3-8}$ cycloalkyl or phenyl or, $R^6$ is $C_{1-5}$ unbranched or branched alkyl or the side chain of a naturally occurring amino acid.

22. The method according to claim 20 wherein $R^2$ is $COCH(R^6)NH_2$ and $R^6$ is selected from the group consisting of $C_{1-5}$ unbranched or branched alkyl or $CH_2Ph$.

23. The method of claim 15 wherein $R^3$ and $R^4$ both are hydrogen.

24. The method of claim 15 wherein $R^1$ is hydrogen and $R^2$, $R^3$ and $R^4$ are independently selected from the group consisting of $COR^5$, $C(=O)OR^5$, $C(=O)SR5$.

25. The method of claim 15 wherein $R^1$ is hydrogen, $R^2$ is selected from the group consisting of $COR^5$, $C(=O)OR^5$, $C(=O)SR^5$ and $COCH(R^6)NHR^7$, and $R^3$ and $R^4$ taken together are selected from the group consisting of $CH_2$, $C(CH_3)_2$ and $CHPh$.

26. The method of claim 15 wherein $R^1$ and $R^2$ are hydrogen and $R^3$ and $R^4$ are independently selected from the group consisting of $COR^5$, $C(=O)OR^5$, $C(=O)SR^5$ and $COCH(R^6)NHR^7$ wherein $R^7$ is hydrogen.

27. The method of claim 15 wherein $R^1$ and $R^2$ are selected from the group consisting of $COR^5$, $C(=O)OR^5$, $C(=O)SR^5$ and $COCH(R^6)NHR^7$, and $R^3$ and $R^4$ taken together are selected from the group consisting of $CH_2$, $C(CH_3)_2$ and $CHPh$.

28. The method of claim 15 wherein the compound is delivered in a dose of between 1 and 100 mg/kg of body weight of the patient per day.

29. The method of claim 15 wherein the mammal is a human.

30. The method of claim 15 further comprising administering at least one immune system modulator and/or at least one antiviral agent that inhibits replication of HCV.

31. The method of claim 30 further comprising administering an immune system modulator.

32. The method of claim 31 wherein the immune system modulator is an interferon, interleukin, tumor necrosis factor or colony stimulating factor or an anti-inflammatory agent.

33. The method of claim 32 wherein the immune system modulator is an interferon or chemically derivatized interferon.

34. The method of claim 33 wherein the immune system modulator is interferon-α or chemically derivatized interferon-α.

35. The method of claim 30 further comprising administering at least one other antiviral agent.

36. The method of claim 35 where the antiviral compound is selected from the group consisting of an HCV protease inhibitor, another HCV polymerase inhibitor, an HCV helicase inhibitor, an HCV primase inhibitor and an HCV fusion inhibitor.

37. A pharmaceutical composition comprising a therapeutically effective quantity of a compound of formula I

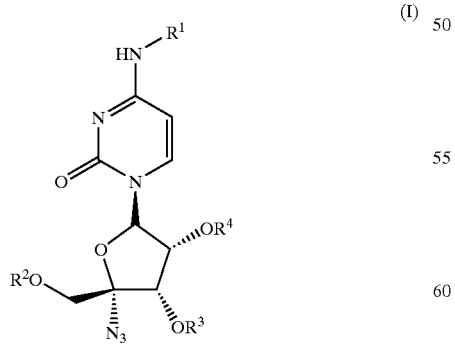

(I)

wherein:
$R^1$ and $R^2$ are independently selected from the group consisting of hydrogen, $COR^5$, $C(=O)OR^5$, $C(=O)SR^5$, $C(=O)NHR^5$ and $COCH(R^6)NHR^7$;

$R^3$ and $R^4$ are independently selected from the group consisting of hydrogen, $COR^5$, $C(=O)OR^5$, $C(=O)SR^5$ and $COCH(R^6)NHR^7$; or, $R^3$ and $R^4$ taken together are selected from the group consisting of $CH_2$, $C(CH_3)_2$ and $CHPh$;

$R^5$ is independently selected from the group consisting of $C_{1-8}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, alkyl substituted $C_{3-8}$ cycloalkyl phenyl, phenyl optionally substituted with one to three substituents independently selected from the group consisting of halo, lower alkyl, lower alkoxy, lower thioalkyl, lower alkyl sulfinyl, lower alkyl sulfonyl, nitro, cyano, $CH_2Ph$ wherein in phenyl ring is optionally substituted as described above, and $CH_2OPh$ wherein in phenyl ring is optionally substituted as described above;

$R^6$ is independently selected from the group consisting of the side chains of naturally occurring amino acids and $C_{1-5}$ unbranched or branched alkyl;

$R^7$ is selected from the group consisting of hydrogen, $R^5OCO$; or, $R^6$ and $R^7$ taken together are $(CH_2)_3$; and, hydrates, solvates, clathrates and acid addition salts thereof; in combination with one or more pharmaceutically acceptable carriers and excipients, with the proviso that at least one of $R^1$, $R^2$, $R^3$, or $R^4$ is other than hydrogen.

38. A process for converting an N-acyl cytidine compound IVa to a cytidine compound IVb by selective cleavage of an N-acyl moiety from IVa wherein:

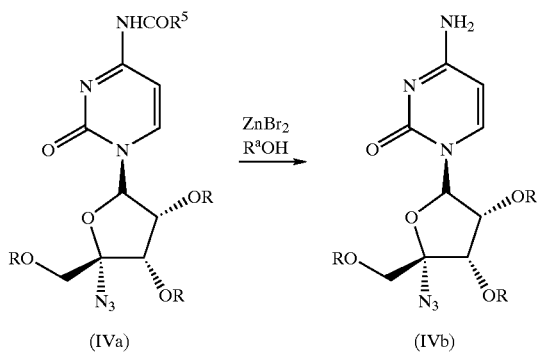

R is independently selected from the group consisting of hydrogen, $COR^5$, $C(=O)OR^5$, $C(=O)SR^5$, $C(=O)NHR^5$ and $COCH(R^6)NHR^7$;

$R^5$ is independently selected from the group consisting of $C_{1-18}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, alkyl substituted $C_{3-8}$ cycloalkyl phenyl, phenyl optionally substituted with one to three substituents independently selected from the group consisting of halo, lower alkyl, lower alkoxy, lower thioalkyl, lower alkyl sulfinyl, lower alkyl sulfonyl, nitro, cyano, $CH_2Ph$ wherein in phenyl ring is optionally substituted as described above, and $CH_2OPh$ wherein in phenyl ring is optionally substituted as described above;

$R^6$ is independently selected from the group consisting of the side chains of naturally occurring amino acids and $C_{1-5}$ unbranched or branched alkyl;

$R^7$ is selected from the group consisting of hydrogen, $R^5OCO$; or, $R^6$ and $R^7$ together are $(CH_2)_3$;

said process comprising contacting a solution of said N-acyl pyrimidine nucleoside with $ZnBr_2$ in a protic solvent $R^bOH$ wherein $R^a$ is hydrogen or $C_{1-4}$ alkyl.

39. A process according to claim 38 wherein said protic solvent is methanol.

* * * * *